US006979467B1

(12) United States Patent
Garces Garces et al.

(10) Patent No.: US 6,979,467 B1
(45) Date of Patent: *Dec. 27, 2005

(54) MICROCAPSULES IV

(75) Inventors: Josep Garces Garces, Barcelona (ES); Josep-Lluis Viladot Petit, Barcelona (ES)

(73) Assignee: Cognis Iberia S.L., Barcelona (ES)

(*) Notice: Subject to any disclaimer, the term of this patent is extended or adjusted under 35 U.S.C. 154(b) by 489 days.

This patent is subject to a terminal disclaimer.

(21) Appl. No.: 10/018,922

(22) PCT Filed: Jun. 23, 2000

(86) PCT No.: PCT/EP00/05810

§ 371 (c)(1), (2), (4) Date: Apr. 18, 2002

(87) PCT Pub. No.: WO01/01929

PCT Pub. Date: Jan. 11, 2001

(30) Foreign Application Priority Data

Jul. 2, 1909 (EP) .................................. 99112668

(51) Int. Cl.$^7$ ........................... A61K 9/14; A61K 9/50; A61K 9/127; B01J 13/02
(52) U.S. Cl. ................. 424/499; 424/450; 424/489; 424/490; 264/4.1; 264/4.33; 264/4.6
(58) Field of Search ............................. 424/450, 451, 424/455, 456, 489, 499, 490; 264/4.1, 4.33, 264/4.6

(56) References Cited

U.S. PATENT DOCUMENTS

| 4,172,887 | A |   | 10/1979 | Vanlerberghe et al. |
| 4,765,976 | A |   | 8/1988 | Grollier et al. |
| 5,008,032 | A |   | 4/1991 | Diessel et al. |
| 5,089,272 | A |   | 2/1992 | Shioya et al. |
| 5,705,169 | A |   | 1/1998 | Stein et al. |
| 5,730,960 | A |   | 3/1998 | Stein et al. |
| 5,753,264 | A |   | 5/1998 | Magdassi et al. |
| 5,827,531 | A | * | 10/1998 | Morrison et al. ........... 424/450 |
| 5,855,904 | A |   | 1/1999 | Chung et al. |
| 5,962,663 | A |   | 10/1999 | Wachter et al. |
| 6,037,487 | A |   | 3/2000 | Habeck et al. |
| 6,193,960 | B1 |   | 2/2001 | Metzger et al. |
| 6,733,790 | B1 | * | 5/2004 | Garces Garces ............. 424/497 |
| 6,818,296 | B1 | * | 11/2004 | Garces Garces et al. 428/402.2 |
| 2003/0147963 | A1 | * | 8/2003 | De Moragas et al. ....... 424/488 |
| 2004/0213997 | A1 | * | 10/2004 | Bonastre Gilabert et al. .... 428/402 |

FOREIGN PATENT DOCUMENTS

| CA | 2101079 | 8/1949 |
| DE | 1 165 574 | 3/1964 |
| DE | 20 24 051 | 12/1971 |
| DE | 0 367 049 | 2/1994 |
| DE | 37 13 099 | 2/1996 |
| DE | 44 42 987 | 6/1996 |
| DE | 195 37 001 | 3/1997 |
| DE | 196 04 180 | 8/1997 |
| DE | 197 12 033 | 9/1998 |
| DE | 197 12 978 | 10/1998 |
| DE | 198 45 246 | 6/1999 |
| EP | 0 152 898 A2 * | 8/1985 |
| EP | 0 237 542 | 9/1987 |
| EP | 0 237 542 B1 * | 1/1991 |
| EP | 0 622 451 | 11/1994 |
| EP | 0 152 898 | 8/1995 |
| EP | 0 693 471 | 1/1996 |
| EP | 0 694 521 | 1/1996 |
| EP | 0 818 450 | 1/1998 |
| FR | 2 252 840 | 8/1975 |
| FR | 2 699 545 | 6/1994 |
| FR | 2 701 266 | 8/1994 |
| GB | 962919 | 7/1964 |
| GB | 1 333 475 | 10/1973 |
| JP | 01018440 | 1/1989 |
| JP | 07258087 | 10/1995 |
| WO | 98/43609 | 10/1998 |

OTHER PUBLICATIONS

Falbe, "Surfactant in Consumer Products", Springer Verlag, Berlin, (1987), pp. 54-124.
Falbe, "Katalysatoren, Tenside und Mineralöladditive" (Catalysts, Surfactants and Mineral Oil Additives), Thieme Verlag, Stuttgart, (1978), pp. 123-217.
Finkel, "Formulierung kosmetischer Sonnenschutzmittel", SÖFW-Journal, vol. 122, (1996), pp. 543-546 & 548.
"Kosmetische Färbemittel", Farbstoffkommission der Deutschen Forschungsgemeinschaft, Verlag Chemie, Weinheim, (1984). pp. 81-106.
"Ullmann's Encyclopedia of Industrial Chemistry", 5$^{th}$ Ed., vol. A6, Weinheim, Verlag Chemie, (1986), pp. 231-232.
Gesslein, et al., "Chitosan, a gift from the sea", HAPPI, vol. 27 (Oct., 1990), pp. 57 & 59.

(Continued)

Primary Examiner—Thurman K. Page
Assistant Examiner—S. Tran
(74) Attorney, Agent, or Firm—Arthur G. Seifert; John F. Daniels

(57) ABSTRACT

A microcapsule having a mean diameter of from about 0.1 to about 5 mm, a membrane and a matrix containing at least one active principle wherein the microcapsule is the product of the process comprising the steps of (a) forming an aqueous matrix by heating an aqueous solution comprised of a gel former, an anionic polymer selected from the group consisting of a salt of alginic acid and an anionic chitosan derivative and active principle; (b) forming a dispersed matrix by adding the aqueous matrix in an oil phase; (c) contacting the dispersed matrix with an aqueous solution of chitosan.

16 Claims, No Drawings

OTHER PUBLICATIONS

Skaugrud, "Chitosan—New Biopolymer For Cosmetics & Drugs", Drug Cosm. Ind., vol. 148, (May, 1991), pp. 24, 26 & 30.

Onsoyen, et al., "Adding Benefits to Cosmetic Formulations by Tailormade Chitosans", Seifen-Öle-Fette-Wachse, vol. 117, (1991), pp. 633-637.

Sannan, et al., "Studies on Chitin, 2", Makromol. Chem., vol. 177, (1976), pp. 3589-3600.

Todd, et al., "Volatile silicone fluids for cosmetic formulations", Cosmetics & Toiletries, vol. 91, (Jan., 1976), pp. 29-32.

* cited by examiner

MICROCAPSULES IV

FIELD OF THE INVENTION

This invention relates generally to the encapsulation of active principles and more particularly to new microcapsules, to a process for their production using various polymers and chitosans and to their use for the production of, for example, surface-active preparations.

PRIOR ART

"Microcapsules" are understood to be spherical aggregates with a diameter of about 0.1 to about 5 mm which contain at least one solid or liquid core surrounded by at least one continuous membrane. More precisely, they are finely dispersed liquid or solid phases coated with film-forming polymers, in the production of which the polymers are deposited onto the material to be encapsulated after emulsification and coacervation or interfacial polymerization. In another process, liquid active principles are absorbed in a matrix ("microsponge") and, as microparticles, may be additionally coated with film-forming polymers. The microscopically small capsules, also known as nanocapsules, can be dried in the same way as powders. Besides single-core microcapsules, there are also multiple-core aggregates, also known as microspheres, which contain two or more cores distributed in the continuous membrane material. In addition, single-core or multiple-core microcapsules may be surrounded by an additional second, third etc. membrane. The membrane may consist of natural, semisynthetic or synthetic materials. Natural membrane materials are, for example, gum arabic, agar agar, agarose, maltodextrins, alginic acid and salts thereof, for example sodium or calcium alginate, fats and fatty acids, cetyl alcohol, collagen, chitosan, lecithins, gelatin, albumin, shellac, polysaccharides, such as starch or dextran, polypeptides, protein hydrolyzates, sucrose and waxes. Semisynthetic membrane materials are inter alia chemically modified celluloses, more particularly cellulose esters and ethers, for example cellulose acetate, ethyl cellulose, hydroxypropyl cellulose, hydroxypropyl methyl cellulose and carboxymethyl cellulose, and starch derivatives, more particularly starch ethers and esters. Synthetic membrane materials are, for example, polymers, such as polyacrylates, polyamides, polyvinyl alcohol or polyvinyl pyrrolidone.

Examples of known microcapsules are the following commercial products (the membrane material is shown in brackets) *Hallcrest Microcapsules* (gelatin, gum arabic), *Coletica Thalaspheres* (maritime collagen), *Lipotec Millicapseln* (alginic acid, agar agar), *Induchem Unispheres* (lactose, microcrystalline cellulose, hydroxypropylmethyl cellulose), *Unicerin C30* (lactose, microcrystalline cellulose, hydroxypropylmethyl cellulose), *Kobo Glycospheres* (modified starch, fatty acid esters, phospholipids), *Softspheres* (modified agar agar) and *Kuhs Probiol Nanospheres* (phospholipids).

Reference is also made in this connection to German patent application DE 19712978 A1 (Henkel) which describes chitosan microspheres obtained by mixing chitosans or chitosan derivatives with oil components and introducing the resulting mixtures into alkalized surfactant solutions. In addition, the use of chitosan as an encapsulating material for tocopherol is known from German patent application DE 19756452 A1 (Henkel).

The active principles are released from the microcapsules by mechanical, thermal, chemical or enzymatic destruction of the membrane, normally during the use of the preparations containing the microcapsules. Disadvantages in this regard are that the microcapsules do not allow controlled release of the active principles from their interior at all or only to an inadequate extent and that the capsules lack stability in the presence of surfactants, especially anionic surfactants. Accordingly, the problem addressed by the present invention was to overcome these disadvantages.

DESCRIPTION OF THE INVENTION

The present invention relates to microcapsules with mean diameters of 0.1 to 5 mm consisting of a membrane and a matrix containing at least one active principle and obtainable by (a) preparing a matrix from gel formers, anionic polymers and active principles, (b) dispersing the matrix in an oil phase and (c) treating the dispersed matrix with aqueous chitosan solutions and removing the oil phase in the process.

It has surprisingly been found that the use of thermogelling natural heteropolysacharides or proteins together with anionic polymers which form membranes in the presence of (cationic) chitosans enables new microcapsules distinguished by distinctly improved surfactant stability to be produced.

The present invention also relates to a process for the production of microcapsules with mean diameters of 0.1 to 5 mm consisting of a membrane and a matrix containing at least one active principle, characterized in that it comprises the steps of (a) preparing a matrix from gel formers, anionic polymers and active principles (b) dispersing the matrix in an oil phase and (c) treating the dispersed matrix with aqueous chitosan solutions and removing the in phase in the process.

Gel Formers

In the context of the invention, preferred gel formers are substances which are capable of forming gels in aqueous solution at temperatures above 40° C. Typical examples of such gel formers are heteropolysaccharides and proteins. Preferred thermogelling heteropolysaccharides are agaroses which may be present in the form of the agar agar obtainable from red algae, even together with up to 30% by weight of non-gel-forming agaropectins. The principal constituent of agaroses are linear polysaccharides of D-galactose and 3,6-anhydro-L-galactose with alternate β-1,3- and β-1,4-glycosidic bonds. The heteropolysaccharides preferably have a molecular weight of 110,000 to 160,000 and are both odorless and tasteless. Suitable alternatives are pectins, xanthans (including xanthan gum) and mixtures thereof. Other preferred types are those which—in 1% by weight aqueous solution—still form gels that do not melt below 80° C. and solidify again above 40° C. Examples from the group of thermogelling proteins are the various gelatines.

Anionic Polymers

Preferred anionic polymers are salts of alginic acid. The alginic acid is a mixture of carboxyl-containing polysaccharides with the following idealized monomer unit:

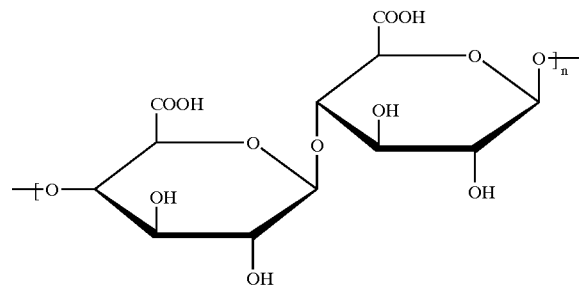

The average molecular weight of the alginic acid or the alginates is in the range from 150,000 to 250,000. Salts of alginic acid and complete and partial neutralization products thereof are understood in particular to be the alkali metal salts, preferably sodium alginate ("algin") and the ammonium and alkaline earth metal salts. Mixed alginates, for example sodium/magnesium or sodium/calcium alginates, are particularly preferred. In an alternative embodiment of the invention, however, anionic chitosan derivatives, for example the carboxylation and above all succinylation products described, for example, in German patent DE 3713099 C2 (L'Oreal) and German patent application DE 19604180 A1 (Henkel) are also suitable for this purpose.

Active Principles

Basically, the choice of the active principles encapsulated in the new microcapsules is not critical. They are preferably substances which are only released by mechanical destruction of the microcapsules. In cases such as these, the function of the microcapsules is to prevent contact between the surrounding environment and the active principle and, hence, chemical reaction and degradation. It may be that the encapsulated substances are not to be released at all and merely serve the purpose of providing the preparation with an aesthetic appearance. This often applies, for example, to dyes. It is of course clear that these forms of use may also exist alongside one another. More particularly, it is possible for example to encapsulate a perfume to be subsequently released together with a pigment which provides the capsule with a particular appearance.

Active Principles for Cosmetic and Pharmaceutical Applications

Typical examples of active principles used in cosmetic and pharmaceutical preparations are surfactants, cosmetic oils, pearlizing waxes, stabilizers, biogenic agents, vitamins, deodorants, antiperspirants, antidandruff agents, UV protection factors, antioxidants, preservatives, insect repellents, self-tanning agents, tyrosine inhibitors (depigmenting agents), perfume oils and dyes.

Anionic, nonionic, cationic and/or amphoteric or zwitterionic surfactants may be encapsulated as surfactants. Typical examples of anionic surfactants are soaps, alkyl benzenesulfonates, alkanesulfonates, olefin sulfonates, alkylether sulfonates, glycerol ether sulfonates, α-methyl ester sulfonates, sulfofatty acids, alkyl sulfates, fatty alcohol ether sulfates, glycerol ether sulfates, fatty acid ether sulfates, hydroxy mixed ether sulfates, monolyceride (ether) sulfates, fatty acid amide (ether) sulfates, mono- and dialkyl sulfosuccinates, mono- and dialkyl sulfosuccinamates, sulfotriglycerides, amide soaps, ether carboxylic acids and salts thereof, fatty acid isethionates, fatty acid sarcosinates, fatty acid taurides, N-acylamino acids such as, for example, acyl lactylates, acyl tartrates, acyl glutamates and acyl aspartates, alkyl oligoglucoside sulfates, protein fatty acid condensates (particularly wheat-based vegetable products) and alkyl (ether) phosphates. If the anionic surfactants contain polyglycol ether chains, they may have a conventional homolog distribution although they preferably have a narrow-range homolog distribution. Typical examples of nonionic surfactants are fatty alcohol polyglycol ethers, alkylphenol polyglycol ethers, fatty acid polyglycol esters, fatty acid amide polyglycol ethers, fatty amine polyglycol ethers, alkoxylated triglycerides, mixed ethers and mixed formals, optionally partly oxidized alk(en)yl oligoglycosides or glucuronic acid derivatives, fatty acid-N-alkyl glucamides, protein hydrolyzates (particularly wheat-based vegetable products), polyol fatty acid esters, sugar esters, sorbitan esters, polysorbates and amine oxides. If the nonionic surfactants contain polyglycol ether chains, they may have a conventional homolog distribution, although they preferably have a narrow-range homolog distribution. Typical examples of cationic surfactants are quaternary ammonium compounds, for example dimethyl distearyl ammonium chloride, and esterquats, more particularly quaternized fatty acid trialkanolamine ester salts. Typical examples of amphoteric or zwitterionic surfactants are alkylbetaines, alkylamidobetaines, aminopropionates, aminoglycinates, imidazolinium betaines and sulfobetaines. The surfactants mentioned are all known compounds. Information on their structure and production can be found in relevant synoptic works, cf. for example J. Falbe (ed.), "Surfactants in Consumer Products", Springer Verlag, Berlin, 1987, pages 54 to 124 or J. Falbe (ed.), "Katalysatoren, Tenside und Mineralöladditive (Catalysts, Surfactants and Mineral Oil Additives)", Thieme Verlag, Stuttgart, 1978, pages 123–217.

Suitable cosmetic oils are, for example, Guerbet alcohols based on fatty alcohols containing 6 to 18 and preferably 8 to 10 carbon atoms, esters of linear $C_{6-22}$ fatty acids with linear $C_{6-22}$ fatty alcohols, esters of branched $C_{6-13}$ carboxylic acids with linear $C_{6-22}$ fatty alcohols such as, for example, myristyl myristate, myristyl palmitate, myristyl stearate, myristyl isostearate, myristyl oleate, myristyl behenate, myristyl erucate, cetyl myristate, cetyl palmitate, cetyl stearate, cetyl isostearate, cetyl oleate, cetyl behenate, cetyl erucate, stearyl myristate, stearyl palmitate, stearyl stearate, stearyl isostearate, stearyl oleate, stearyl behenate, stearyl erucate, isostearyl myristate, isostearyl palmitate, isostearyl stearate, isostearyl isostearate, isostearyl oleate, isostearyl behenate, isostearyl oleate, oleyl myristate, oleyl palmitate, oleyl stearate, oleyl isostearate, oleyl oleate, oleyl behenate, oleyl erucate, behenyl myristate, behenyl palmitate, behenyl stearate, behenyl isostearate, behenyl oleate, behenyl behenate, behenyl erucate, erucyl myristate, erucyl palmitate, erucyl stearate, erucyl isostearate, erucyl oleate, erucyl behenate and erucyl erucate. Also suitable are esters of linear $C_{6-22}$ fatty acids with branched alcohols, more particularly 2-ethyl hexanol, esters of hydroxycarboxylic acids with linear or branched $C_{6-22}$ fatty alcohols, more especially Dioctyl Malate, esters of linear and/or branched fatty acids with polyhydric alcohols (for example propylene glycol, dimer diol or trimer triol) and/or Guerbet alcohols, triglycerides based on $C_{6-10}$ fatty acids, liquid mono/di/triglyceride mixtures based on $C_{6-18}$ fatty acids, esters of $Cr_{6-22}$ fatty alcohols and/or Guerbet alcohols with aromatic carboxylic acids, more particularly benzoic acid, esters of $C_{2-12}$ dicarboxylic acids with linear or branched alcohols containing 1 to 22 carbon atoms or polyols containing 2 to 10 carbon atoms and 2 to 6 hydroxyl groups, vegetable oils, branched primary alcohols, substituted cyclohexanes, linear and branched $C_{6-22}$ fatty alcohol carbonates, Guerbet carbonates, esters of benzoic acid with linear and/or branched $C_{6-22}$ alcohols (for example Finsolv® TN), linear or branched, symmetrical or nonsymmetrical dialkyl ethers containing 6 to 22 carbon atoms per alkyl group, ring opening products of epoxidized fatty acid esters with polyols, silicone oils and/or aliphatic or naphthenic hydrocarbons, for example squalane, squalene or dialkyl cyclohexanes.

Suitable pearlizing waxes are, for example, alkylene glycol esters, especially ethylene glycol distearate; fatty acid alkanolamides, especially cocofatty acid diethanolamide; partial glycerides, especially stearic acid monoglyceride; esters of polybasic, optionally hydroxysubstituted carboxylic acids with fatty alcohols containing 6 to 22 carbon atoms, especially long-chain esters of tartaric acid; fatty compounds, such as for example fatty alcohols, fatty ketones, fatty aldehydes, fatty ethers and fatty carbonates which contain in all at least 24 carbon atoms, especially laurone and distearylether; fatty acids, such as stearic acid, hydroxystearic acid or behenic acid, ring opening products of olefin epoxides containing 12 to 22 carbon atoms with fatty alcohols containing 12 to 22 carbon atoms and/or polyols containing 2 to 15 carbon atoms and 2 to 10 hydroxyl groups and mixtures thereof.

Metal salts of fatty acids such as, for example, magnesium, aluminium and/or zinc stearate or ricinoleate may be used as stabilizers.

In the context of the invention, biogenic agents are, for example, tocopherol, tocopherol acetate, tocopherol palmitate, ascorbic acid, deoxyribonucleic acid, retinol, bisabolol, allantoin, phytantriol, panthenol, AHA acids, koji acid, amino acids, ceramides, pseudoceramides, essential oils, plant extracts and vitamin complexes.

Cosmetic deodorants counteract, mask or eliminate body odors. Body odors are formed through the action of skin bacteria on apocrine perspiration which results in the formation of unpleasant-smelling degradation products. Accordingly, deodorants contain active principles which act as germ inhibitors, enzyme inhibitors, odor absorbers or odor maskers.

Basically, suitable germ inhibitors are any substances which act against gram-positive bacteria such as, for example, 4-hydroxybenzoic acid and salts and esters thereof, N-(4-chlorophenyl)-N'-(3,4-dichlorophenyl)urea, 2,4,4'-trichloro-2'-hydroxydiphenylether (triclosan), 4-chloro-3,5-dimethylphenol, 2,2'-methylene-bis-(6-bromo-4-chlorophenol), 3-methyl-4-(1-methylethyl)-phenol, 2-benzyl-4-chlorophenol, 3-(4-chlorophenoxy)propane-1,2-diol, 3-iodo-2-propinyl butyl carbamate, chlorhexidine, 3,4,4'-trichlorocarbanilide (TTC), antibacterial perfumes, thymol, thyme oil, eugenol, clove oil, menthol, mint oil, farnesol, phenoxyethanol, glycerol monolaurate (GML), diglycerol monocaprate (DMC), salicylic acid-N-alkylamides such as, for example, salicylic acid-n-octyl amide or salicylic acid-n-decyl amide.

Suitable enzyme inhibitors are, for example, esterase inhibitors. Esterase inhibitors are preferably trialkyl citrates, such as trimethyl citrate, tripropyl citrate, triisopropyl citrate, tributyl citrate and, in particular, triethyl citrate (Hydagen® CAT, Henkel KGaA, Dusseldorf, FRG). Esterase inhibitors inhibit enzyme activity and thus reduce odor formation. Other esterase inhibitors are sterol sulfates or phosphates such as, for example, lanosterol, cholesterol, campesterol, stigmasterol and sitosterol sulfate or phosphate, dicarboxylic acids and esters thereof, for example glutaric acid, glutaric acid monoethyl ester, glutaric acid diethyl ester, adipic acid, adipic acid monoethyl ester, adipic acid diethyl ester, malonic acid and malonic acid diethyl ester, hydroxycarboxylic acids and esters thereof, for example citric acid, malic acid, tartaric acid or tartaric acid diethyl ester, and zinc glycinate.

Suitable odor absorbers are substances which are capable of absorbing and largely retaining the odor-forming compounds. They reduce the partial pressure of the individual components and thus also reduce the rate at which they spread. An important requirement in this regard is that perfumes must remain unimpaired. Odor absorbers are not active against bacteria. They contain, for example, a complex zinc salt of ricinoleic acid or special perfumes of largely neutral odor known to the expert as "fixateurs" such as, for example, extracts of labdanum or styrax or certain abietic acid derivatives as their principal component. Odor maskers are perfumes or perfume oils which, besides their odor-masking function, impart their particular perfume note to the deodorants. Suitable perfume oils are, for example, mixtures of natural and synthetic fragrances. Natural fragrances include the extracts of blossoms, stems and leaves, fruits, fruit peel, roots, woods, herbs and grasses, needles and branches, resins and balsams. Animal raw materials, for example civet and beaver, may also be used. Typical synthetic perfume compounds are products of the ester, ether, aldehyde, ketone, alcohol and hydrocarbon type. Examples of perfume compounds of the ester type are benzyl acetate, p-tert.butyl cyclohexylacetate, linalyl acetate, phenyl ethyl acetate, linalyl benzoate, benzyl formate, allyl cyclohexyl propionate, styrallyl propionate and benzyl salicylate. Ethers include, for example, benzyl ethyl ether while aldehydes include, for example, the linear alkanals containing 8 to 18 carbon atoms, citral, citronellal, citronellyloxyacetaldehyde, cyclamen aldehyde, hydroxycitronellal, lilial and bourgeonal. Examples of suitable ketones are the ionones and methyl cedryl ketone. Suitable alcohols are anethol, citronellol, eugenol, isoeugenol, geraniol, linalool, phenylethyl alcohol and terpineol. The hydrocarbons mainly include the terpenes and balsams. However, it is preferred to use mixtures of different perfume compounds which, together, produce an agreeable fragrance. Other suitable perfume oils are essential oils of relatively low volatility which are mostly used as aroma components. Examples are sage oil, camomile oil, clove oil, melissa oil, mint oil, cinnamon leaf oil, lime-blossom oil, juniper berry oil, vetiver oil, olibanum oil, galbanum oil, ladanum oil and lavendin oil. The following are preferably used either individually or in the form of mixtures: bergamot oil, dihydromyrcenol, lilial, lyral, citronellol, phenylethyl alcohol, ahexylcinnamaldehyde, geraniol, benzyl acetone, cyclamen aldehyde, linalool, Boisambrene Forte, Ambroxan, indole, hedione, sandelice, citrus oil, mandarin oil, orange oil, allylamyl glycolate, cyclovertal, lavendin oil, clary oil, β-damascone, geranium oil bourbon, cyclohexyl salicylate, Vertofix Coeur, Iso-E-Super, Fixolide NP, everynl, iraldein gamma, phenylacetic acid, geranyl acetate, benzyl acetate, rose oxide, romilat, irotyl and floramat.

Antiperspirants reduce perspiration and thus counteract underarm wetness and body odor by influencing the activity of the eccrine sweat glands. Aqueous or water-free antiperspirant formulations typically contain the following ingredients:

astringent active principles,
oil components,
nonionic emulsifiers,
co-emulsifiers,
consistency factors,
auxiliaries in the form of, for example, thickeners or complexing agents and/or
nonaqueous solvents such as, for example, ethanol, propylene glycol and/or glycerol.

Suitable astringent active principles of antiperspirants are, above all, salts of aluminium, zirconium or zinc. Suitable antihydrotic agents of this type are, for example, aluminium chloride, aluminium chlorohydrate, aluminium dichlorohydrate, aluminium sesquichlorohydrate and complex compounds thereof, for example with 1,2-propylene glycol, aluminium hydroxyallantoinate, aluminium chloride tartrate, aluminium zirconium trichlorohydrate, aluminium zirconium tetrachlorohydrate, aluminium zirconium pentachlorohydrate and complex compounds thereof, for example with amino acids, such as glycine. Oil-soluble and water-soluble auxiliaries typically encountered in antiperspirants may also be present in relatively small amounts. Oil-soluble auxiliaries such as these include, for example,

- inflammation-inhibiting, skin-protecting or pleasant-smelling essential oils,
- synthetic skin-protecting agents and/or
- oil-soluble perfume oils.

Typical water-soluble additives are, for example, preservatives, water-soluble perfumes, pH adjusters, for example buffer mixtures, water-soluble thickeners, for example water-soluble natural or synthetic polymers such as, for example, xanthan gum, hydroxyethyl cellulose, polyvinyl pyrrolidone or high molecular weight polyethylene oxides.

Suitable antidandruff agents are climbazol, octopirox, ketoconazole and zinc pyrithione.

Examples of UV protection factors are organic substances (light filters) which are liquid or crystalline at room temperature and which are capable of absorbing ultraviolet radiation and of releasing the energy absorbed in the form of longer-wave radiation, for example heat. UV-B filters can be oil-soluble or water-soluble. The following are examples of oil-soluble substances:

- 3-benzylidene camphor or 3-benzylidene norcamphor and derivatives thereof, for example 3-(4-methylbenzylidene)-camphor, as described in EP 0693471 B1;
- 4-aminobenzoic acid derivatives, preferably 4-(dimethylamino)-benzoic acid-2-ethylhexyl ester, 4-(dimethylamino)-benzoic acid-2-octyl ester and 4-(dimethylamino)-benzoic acid amyl ester;
- esters of cinnamic acid, preferably 4-methoxycinnamic acid-2-ethylhexyl ester, 4-methoxycinnamic acid propyl ester, 4-methoxycinnamic acid isoamyl ester, 2-cyano-3,3-phenylcinnamic acid-2-ethylhexyl ester (Octocrylene);
- esters of salicylic acid, preferably salicylic acid-2-ethylhexyl ester, salicylic acid-4-isopropylbenzyl ester, salicylic acid homomenthyl ester;
- derivatives of benzophenone, preferably 2-hydroxy-4-methoxybenzophenone, 2-hydroxy-4-methoxy-4'-methylbenzophenone, 2,2'-dihydroxy-4-methoxybenzophenone;
- esters of benzalmalonic acid, preferably 4-methoxybenzalmalonic acid di-2-ethylhexyl ester;
- triazine derivatives such as, for example, 2,4,6-trianilino-(p-carbo-2'-ethyl-1'-hexyloxy)-1,3,5-triazine and Octyl Triazone, as described in EP 0 818 450 A1, or Dioctyl Butamido Triazine (Uvasorb®) HEB);
- propane-1,3-diones such as, for example, 1-(4-tert.butylphenyl)-3-(4'-methoxyphenyl)-propane-1,3-dione;
- ketotricyclo(5.2.1.0)decane derivatives, as described in EP 0 694 521 B1.

Suitable water-soluble substances are

- 2-phenylbenzimidazole-5-sulfonic acid and alkali metal, alkaline earth metal, ammonium, alkylammonium, alkanolammonium and glucammonium salts thereof;
- sulfonic acid derivatives of benzophenones, preferably 2-hydroxy-4-methoxybenzophenone-5-sulfonic acid and salts thereof;
- sulfonic acid derivatives of 3-benzylidene camphor such as, for example, 4-(2-oxo-3-bornylidenemethyl)-benzene sulfonic acid and 2-methyl-5-(2-oxo-3-bornylidene)-sulfonic acid and salts thereof.

Typical UV-A filters are, in particular, derivatives of benzoyl methane such as, for example 1-(4'-tert.butylphenyl)-3-(4'-methoxyphenyl)-propane 1,3-dione, 4-tert-butyl-4'-methoxydibenzoylmethane (Parsol 1789), 1-phenyl-3-(4'-isopropylphenyl)-propane-1,3-dione and the eneamine compounds described in DE 19712033 A1 (BASF). The UV-A and UV-B filters may of course also be used in the form of mixtures. Besides the soluble substances mentioned, insoluble pigments, i.e. finely dispersed metal oxides or salts, may also be used for this purpose. Examples of suitable metal oxides are, in particular, zinc oxide and titanium dioxide and also oxides of iron, zirconium, silicon, manganese, aluminium and cerium and mixtures thereof. Silicates (talcum), barium sulfate and zinc stearate may be used as salts. The oxides and salts are used in the form of the pigments for skin-care and skin-protecting emulsions and decorative cosmetics. The particles should have an average diameter of less than 100 nm, preferably from 5 to 50 nm and more preferably from 15 to 30 nm. They may be spherical in shape although ellipsoidal particles or other nonspherical particles may also be used. The pigments may also be surfacetreated, i.e. hydrophilicized or hydrophobicized. Typical examples are coated titanium dioxides such as, for example, Titandioxid T 805 (Degussa) or Eusolex® T2000 (Merck). Suitable hydrophobic coating materials are, above all, silicones and particularly trialkoxyoctyl silanes or simethicones. So-called micro- or nanopigments are preferably used in sun protection products. Micronized zinc oxide is preferably used. Other suitable UV filters can be found in P. Finkel's review in SÖFW-Journal 122, 543 (1996).

Besides the two above-mentioned groups of primary protection factors, secondary protection factors of the antioxidant type may also be used. Secondary sun protection factors of the antioxidant type interrupt the photochemical reaction chain which is initiated when UV rays penetrate into the skin. Typical examples of suitable antioxidants are amino acids (for example glycine, histidine, tyrosine, tryptophane) and derivatives thereof, imidazoles (for example urocanic acid) and derivatives thereof, peptides, such as D,L-carnosine, D-carnosine, L-carnosine and derivatives thereof (for example anserine), carotinoids, carotenes (for example α-carotene, β-carotene, lycopene) and derivatives thereof, chlorogenic acid and derivatives thereof, liponic acid and derivatives thereof (for example dihydroliponic acid), aurothioglucose, propylthiouracil and other thiols (for example thioredoxine, glutathione, cysteine, cystine, cystamine and glycosyl, N-acetyl, methyl, ethyl, propyl, amyl, butyl and lauryl, palmitoyl, oleyl, γ-linoleyl, cholesteryl and glyceryl esters thereof) and their salts, dilaurylthiodipropionate, distearylthiodipropionate, thiodipropionic acid and derivatives thereof (esters, ethers, peptides, lipids, nucleotides, nucleosides and salts) and sulfoximine compounds (for example butionine sulfoximines, homocysteine sulfoximine, butionine sulfones, penta-, hexa- and hepta-thionine sulfoximine) in very small compatible dosages (for example pmole to µmole/kg), also (metal) chelators (for example α-hydroxyfatty acids, palmitic acid, phytic acid, lactoferrine), α-hydroxy acids (for example citric acid, lactic acid, malic acid), humic acid, bile acid, bile extracts, bilirubin, biliverdin, EDTA, EGTA and derivatives thereof, unsaturated fatty acids and derivatives thereof (for example γ-linolenic acid, linoleic acid, oleic acid), folic acid and derivatives thereof, ubiquinone and ubiquinol and derivatives thereof, vitamin C and derivatives thereof (for example ascorbyl palmitate, Mg ascorbyl phosphate, ascorbyl acetate), tocopherols and derivatives (for example vitamin E acetate), vitamin A and derivatives (vitamin A palmitate) and coniferyl benzoate of benzoin resin, rutinic acid and derivatives thereof, α-glycosyl rutin, ferulic acid, furfurylidene glucitol, carnosine, butyl hydroxytoluene, butyl hydroxyanisole, nordihydroguaiac resin acid, nordihydroguaiaretic acid, trihydroxybutyrophenone, uric acid and derivatives thereof, mannose and derivatives thereof, Superoxid-Dismutase, zinc and derivatives thereof (for example ZnO, $ZnSO_4$), selenium and derivatives thereof (for example selenium methionine), stilbenes and derivatives thereof (for example stilbene oxide, trans-stilbene oxide) and derivatives of these active principles suitable for the purposes of the invention (salts, esters, ethers, sugars, nucleotides, nucleosides, peptides and lipids).

Suitable preservatives are, for example, phenoxyethanol, formaldehyde solution, parabens, pentanediol or sorbic acid and the other classes of compounds listed in Appendix 6, Parts A and B of the Kosmetikverordnung ("Cosmetics Directive"). Suitable insect repellents are N,N-diethyl-m-toluamide, pentane-1,2-diol or Ethyl Butylacetylaminopropionate. A suitable self-tanning agent is dihydroxyacetone. Tyrosine inhibitors, which prevent the formation of melanin and are used in depigmenting formulations, are for example arbutin, koji acid, coumaric acid and ascorbic acid (vitamin C)

Suitable perfume oils are mixtures of natural and synthetic perfumes. Natural perfumes include the extracts of blossoms (lily, lavender, rose, jasmine, neroli, ylang—ylang), stems and leaves (geranium, patchouli, petitgrain), fruits (anise, coriander, caraway, juniper), fruit peel (bergamot, lemon, orange), roots (nutmeg, angelica, celery, cardamon, costus, iris, calmus), woods (pinewood, sandalwood, guaiac wood, cedarwood, rosewood), herbs and grasses (tarragon, lemon grass, sage, thyme), needles and branches (spruce, fir, pine, dwarf pine), resins and balsams (galbanum, elemi, benzoin, myrrh, olibanum, opoponax). Animal raw materials, for example civet and beaver, may also be used. Typical synthetic perfume compounds are products of the ester, ether, aldehyde, ketone, alcohol and hydrocarbon type. Examples of perfume compounds of the ester type are benzyl acetate, phenoxyethyl isobutyrate, p-tert.butyl cyclohexylacetate, linalyl acetate, dimethyl benzyl carbinyl acetate, phenyl ethyl acetate, linalyl benzoate, benzyl formate, ethylmethyl phenyl glycinate, allyl cyclohexyl propionate, styrallyl propionate and benzyl salicylate. Ethers include, for example, benzyl ethyl ether while aldehydes include, for example, the linear alkanals containing 8 to 18 carbon atoms, citral, citronellal, citronellyloxyacetaldehyde, cyclamen aldehyde, hydroxycitronellal, lilial and bourgeonal. Examples of suitable ketones are the ionones, α-isomethylionone and methyl cedryl ketone. Suitable alcohols are anethol, citronellol, eugenol, isoeugenol, geraniol, linalool, phenylethyl alcohol and terpineol. The hydrocarbons mainly include the terpenes and balsams. However, it is preferred to use mixtures of different perfume compounds which, together, produce an agreeable fragrance. Other suitable perfume oils are essential oils of relatively low volatility which are mostly used as aroma components. Examples are sage oil, camomile oil, clove oil, melissa oil, mint oil, cinnamon leaf oil, lime-blossom oil, juniper berry oil, vetiver oil, olibanum oil, galbanum oil, ladanum oil and lavendin oil. The following are preferably used either individually or in the form of mixtures: bergamot oil, dihydromyrcenol, lilial, lyral, citronellol, phenylethyl alcohol, α-hexylcinnamaldehyde, geraniol, benzyl acetone, cyclamen aldehyde, linalool, Boisambrene Forte, Ambroxan, indole, hedione, sandelice, citrus oil, mandarin oil, orange oil, allylamyl glycolate, cyclovertal, lavendin oil, clary oil, β-damascone, geranium oil bourbon, cyclohexyl salicylate, Vertofix Coeur, Iso-E-Super, Fixolide NP, evernyl, iraldein gamma, phenylacetic acid, geranyl acetate, benzyl acetate, rose oxide, romillat, irotyl and floramat.

Suitable dyes are any of the substances suitable and approved for cosmetic purposes as listed, for example, in the publication "Kosmetische Fätrbemittel" of the Farbstoffkommission der Deutschen Forschungsgemeinschaft, Verlag Chemie, Weinheim, 1984, pages 81 to 106. These active principles may also be present in the capsules solely for aesthetic reasons, i.e are not intended for controlled release.

Active Principles for Detergent Applications

Where microcapsules are used in the field of detergents, particularly laundry detergents, it is again desirable to prevent the various ingredients from coming into contact with one another. Thus, it is appropriate to encapsulate chemically sensitive substances, such as perfume oils or optical brighteners for example, in order to safeguard their activity, for example in chlorine or peroxide bleach liquors, even in the event of prolonged storage. However, use is also made of the fact that the bleaching of textiles generally takes place during rather than at the beginning of the washing process, the release delayed by mechanical action on the microcapsules ensuring that the bleaching agents develop their full effect at the right time. Accordingly, active principles to be encapsulated for detergent applications include, above all, bleaching agents, bleach activators, enzymes, redeposition inhibitors, optical brighteners and (chlorine- and peroxide-stable) perfumes and dyes.

Among the compounds yielding hydrogen peroxide in water which are used as bleaching agents, sodium perborate tetrahydrate and sodium perborate monohydrate are particularly important. Other suitable bleaching agents are, for example, peroxycarbonate, citrate perhydrates and salts of peracids, such as perbenzoates, peroxyphthalates or diperoxydodecanedioic acid. They are normally used in quantities of 8 to 25% by weight. Sodium perborate monohydrate is preferred and is used in quantities of 10 to 20% by weight and preferably in quantities of 10 to 15% by weight. By virtue of its ability to bind free water to form the tetrahydrate, it contributes towards increasing the stability of the detergent.

Examples of suitable bleach activators are N-acyl and O-acyl compounds which form organic peracids with hydrogen peroxide, preferably N,N'-tetraacylated diamines, also carboxylic anhydrides and esters of polyols, such as glucose pentaacetate. The bleach activator content of bleach-containing compositions is in the usual range, i.e. preferably between 1 and 10% by weight and more preferably between 3 and 8% by weight. Particularly preferred bleach activators are N,N,N',N'-tetraacetyl ethylenediamine and 1,5-diacetyl-2,4-dioxohexahydro-1,3,5-triazine.

Suitable enzymes are those from the class of proteases, lipases, amylases, cellulases and mixtures thereof. Enzymes obtained from bacterial strains or fungi, such as *Bacillus subtilis, Bacillus licheniformis* and *Streptomyces griseus*, are particularly suitable. Proteases of the subtilisin type are preferably used, proteases obtained from *Bacillus lentus* being particularly preferred. They may be used in quantities of about 0.2 to about 2% by weight. The enzymes may be adsorbed onto supports and/or encapsulated in membrane materials to protect them against premature decomposition. In addition to the monohydric and polyhydric alcohols and the phosphonates, the compositions may contain other enzyme stabilizers. For example, 0.5 to 1% by weight of sodium formate may be used. It is also possible to use proteases which are stabilized with soluble calcium salts and which have a calcium content of preferably about 1.2% by weight, based on the enzyme. However, it is of particular advantage to use boron compounds, for example boric acid, boron oxide, borax and other alkali metal borates, such as the salts of orthoboric acid ($H_3BO_3$), metaboric acid ($HBO_2$) and pyroboric acid (tetraboric acid $H_2B_4O_7$).

Suitable redeposition inhibitors are water-soluble, generally organic colloids, for example the water-soluble salts of polymeric carboxylic acids, glue, gelatine, salts of ether carboxylic acids or ether sulfonic acids of starch or cellulose or salts of acidic sulfuric acid esters of cellulose or starch. Water-soluble polyamides containing acidic groups are also suitable for this purpose. Soluble starch preparations and other starch products than those mentioned above, for example degraded starch, aldehyde starches, etc., may also be used. Polyvinyl pyrrolidone is also suitable. However, cellulose ethers, such as carboxymethyl cellulose, methyl cellulose, hydroxyalkyl cellulose, and mixed ethers, such as methyl hydroxyethyl cellulose, methyl hydroxypropyl cellulose, methyl carboxymethyl cellulose and mixtures thereof, and polyvinyl pyrrolidone are also preferably used, for example in quantities of 0.1 to 99% by weight and preferably 1 to 5% by weight, based on the composition.

Derivatives of diaminostilbene disulfonic acid or alkali metal salts thereof may be used as optical brighteners. Suitable optical brighteners are, for example, salts of 4,4'-bis-(2-anilino-4-morpholino-1,3,5-triazinyl-6-amino)-stilbene-2,2'-disulfonic acid or compounds of similar structure which, instead of the morpholino group, contain a diethanolamino group, a methylamino group, an anilino group or a 2-methoxyethylamino group. Brighteners of the substituted diphenyl styryl type, for example alkali metal salts of 4,4'-bis-(2-sulfostyryl)-diphenyl, 4,4'-bis-(4-chloro-3-sulfostyryl)diphenyl or 4-(4-chlorostyryl)-4'-(2-sulfostyryl)-diphenyl, may also be present. Mixtures of the brighteners mentioned above may also be used. A particularly preferred dye is Tinolux® (a product of Ciba-Geigy).

Examples of perfumes stable to active chlorine are: citronellol (3,7-dimethyl-6-octen-1-ol), dimethyl octanol (3,7-dimethyl-1-octanol), hydroxycitronellol (3,7-dimethyloctane-1,7-diol), mugol (3,7-dimethyl-4,6-octatrien-3-ol), myrcenol (2-methyl-6-methylene-7-octen-2-ol), terpinolene (p-mentho-1,4-(8)-diene), ethyl-2-methyl butyrate, phenyl propyl alcohol, galaxolide (1,3,4,6,7,8-hexahydro-4,6,6,7,8,8-hexamethyl cyclopental-2-benzopyran), tonalide (7-acetyl-1,1,3,4,4,6-hexamethyl tetrahydronaphthalene), rose oxide, linalol oxide, 2,6-dimethyl-3-octanol, tetrahydroethyl linalool, tetrahydroethyl linalyl acetate, o-sec.-butyl cyclohexyl acetate and isolone diphorenepoxide and also isoborneal, dihydroterpineol, isobornyl acetate, dihydroterpenyl acetate). Other suitable perfumes are the substances mentioned columns 3 and 4 of European patent application EP 0622451 A1 (Procter & Gamble).

Besides inorganic types, such as iron or bismuth oxides for example, suitable pigments are, above all, green chlorophthalocyanines (Pigmosol® Grün, Hostaphine® Grun), yellow Solar Yellow BG 300 (Sandoz), blue chlorophthalocyanine (Hostaphine® Blau) or Cosmenyl® Blau.

Oil Phase

The oil phase in which the matrix is finely dispersed may be formed by any of the cosmetic oil components mentioned above under the heading "active principles". It is preferably a paraffin or vegetable oil, the oil phase normally making up 2 to 5 times the volume of the matrix.

Chitosans

The function of the negatively charged chitosans is to form membranes with the anionic polymers. Chitosans are biopolymers which belong to the group of hydrocolloids. Chemically, they are partly deacetylated chitins differing in their molecular weights which contain the following—idealized—monomer unit:

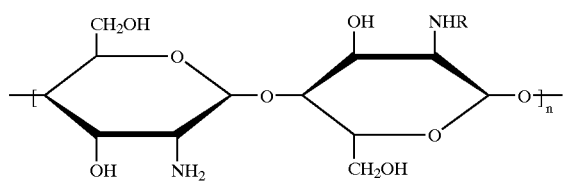

In contrast to most hydrocolloids, which are negatively charged at biological pH values, chitosans are cationic biopolymers under these conditions. The positively charged chitosans are capable of interacting with oppositely charged surfaces and are therefore used in cosmetic hair-care and body-care products and pharmaceutical preparations (cf. Ullmann's Encyclopedia of Industrial Chemistry, 5th Ed., Vol. A6, Weinheim, Verlag Chemie, 1986, pages 231–332). Overviews of this subject have also been published, for example, by B. Gesslein et al. in HAPPI 27, 57 (1990), O. Skaugrud in Drug Cosm. Ind. 148, 24 (1991) and E. Onsoyen et al. in Seifen-Öle-Fette-Wachse 117, 633 (1991). Chitosans are produced from chitin, preferably from the shell residues of crustaceans which are available in large quantities as inexpensive raw materials. In a process described for the first time by Hackmann et al., the chitin is normally first deproteinized by addition of bases, demineralized by addition of mineral acids and, finally, deacetylated by addition of strong bases, the molecular weights being distributed over a broad spectrum. Corresponding processes are known, for example, from Makromol. Chem. 177, 3589 (1976) or French patent application FR 2701266 A. Preferred types are those which are disclosed in German patent applications DE 4442987 A1 and DE 19537001 A1 (Henkel) and which have an average molecular weight of 10,000 to 500,000 dalton or 800,000 to 1,200,000 dalton and/or a Brookfield viscosity (1% by weight in glycolic acid) below 5,000 mPas, a degree of deacetylation of 80 to 88% and an ash content of less than 0.3% by weight. In the interests of better solubility in water, the chitosans are generally used in the form of their salts, preferably as glycolates.

Production Process

To produce the new microcapsules, a 1 to 10 and preferably 2 to 5% by weight aqueous solution of the gel former, preferably agar agar, is normally prepared and heated under reflux. A second aqueous solution containing the anionic polymers in quantities of 0.1 to 2 and preferably 0.25 to 0.5% by weight and the active principle in quantities of 0.1 to 25 and preferably 0.25 to 10% by weight is added in the boiling heat, preferably at 80 to 100° C.; this mixture is called the matrix. Accordingly, the charging of the microcapsules with active principles may also comprise 0.1 to 25% by weight, based on the weight of the capsules. If desired, water-insoluble constituents, for example inorganic pigments, may also be added at this stage to adjust viscosity, generally in the form of aqueous or aqueous/alcoholic dispersions. In addition, to emulsify or disperse the active principles, it can be useful to add emulsifiers and/or solubilizers to the matrix.

Suitable emulsifiers are, for example, nonionic surfactants from at least one of the following groups:

products of the addition of 2 to 30 moles of ethylene oxide and/or 0 to 5 moles of propylene oxide onto linear $C_{8-22}$ fatty alcohols, $C_{12-22}$ fatty acids and alkyl phenols containing 8 to 15 carbon atoms in the alkyl group and alkylamines containing 8 to 22 carbon atoms in the alkyl group;

alkyl and/or alkenyl oligoglycosides containing 8 to 22 carbon atoms in the alkyl group and ethoxylated analogs thereof;

addition products of 1 to 15 moles of ethylene oxide with castor oil and/or hydrogenated castor oil;

addition products of 15 to 60 moles of ethylene oxide with castor oil and/or hydrogenated castor oil;

partial esters of glycerol and/or sorbitan with unsaturated, linear or saturated, branched fatty acids containing 12 to 22 carbon atoms and/or hydroxycarboxylic acids containing 3 to 18 carbon atoms and addition products thereof with 1 to 30 moles of ethylene oxide;

partial esters of polyglycerol (average degree of self-condensation 2 to 8), polyethylene glycol (molecular weight 400 to 5000), trimethylolpropane, pentaerythritol, sugar alcohols (for example sorbitol), alkyl glucosides (for example methyl glucoside, butyl glucoside, lauryl glucoside) and polyglucosides (for example cellulose) with saturated and/or unsaturated, linear or branched fatty acids containing 12 to 22 carbon atoms and/or hydroxycarboxylic acids containing 3 to 18 carbon atoms and addition products thereof with 1 to 30 moles of ethylene oxide;

mixed esters of pentaerythritol, fatty acids, citric acid and fatty alcohol according to DE-PS 11 65 574 and/or mixed esters of fatty acids containing 6 to 22 carbon atoms, methyl glucose and polyols, preferably glycerol or polyglycerol, mono-, di- and trialkyl phosphates and mono-, di- and/or tri-PEG-alkyl phosphates and salts thereof, wool wax alcohols, polysiloxane/polyalkyl/polyether copolymers and corresponding derivatives, polyalkylene glycols and glycerol carbonate.

The addition products of ethylene oxide and/or propylene oxide with fatty alcohols, fatty acids, alkylphenols or with castor oil are known commercially available products. They are homolog mixtures of which the average degree of alkoxylation corresponds to the ratio between the quantities of ethylene oxide and/or propylene oxide and substrate with which the addition reaction is carried out. $C_{12/18}$ fatty acid monoesters and diesters of addition products of ethylene oxide with glycerol are known as refatting agents for cosmetic formulations from DE-PS 20 24 051.

Alkyl and/or alkenyl oligoglycosides, their production and their use are known from the prior art. They are produced in particular by reacting glucose or oligosaccharides with primary alcohols containing 8 to 18 carbon atoms. So far as the glucoside unit is concerned, both monoglycosides in which a cyclic sugar unit is attached to the fatty alcohol by a glycoside bond and oligomeric glycosides with a degree of oligomerization of preferably up to about 8 are suitable. The degree of oligomerization is a statistical mean value on which the homolog distribution typical of such technical products is based.

Typical examples of suitable partial glycerides are hydroxystearic acid monoglyceride, hydroxystearic acid diglyceride, isostearic acid monoglyceride, isostearic acid diglyceride, oleic acid monoglyceride, oleic acid diglyceride, ricinoleic acid monoglyceride, ricinoleic acid diglyceride, linoleic acid monoglyceride, linoleic acid diglyceride, linolenic acid monoglyceride, linolenic acid diglyceride, erucic acid monoglyceride, erucic acid diglyceride, tartaric acid monoglyceride, tartaric acid diglyceride, citric acid monoglyceride, citric acid diglyceride, malic acid monoglyceride, malic acid diglyceride and technical mixtures thereof which may still contain small quantities of triglyceride from the production process. Addition products of 1 to 30 and preferably 5 to 10 moles of ethylene oxide with the partial glycerides mentioned are also suitable.

Suitable sorbitan esters are sorbitan monoisostearate, sorbitan sesquiisostearate, sorbitan diisostearate, sorbitan triisostearate, sorbitan monooleate, sorbitan sesquioleate, sorbitan dioleate, sorbitan trioleate, sorbitan monoerucate, sorbitan sesquierucate, sorbitan dierucate, sorbitan trierucate, sorbitan monoricinoleate, sorbitan sesquiricinoleate, sorbitan diricinoleate, sorbitan triricinoleate, sorbitan monohydroxystearate, sorbitan sesquihydroxystearate, sorbitan dihydroxystearate, sorbitan trihydroxystearate, sorbitan monotartrate, sorbitan sesquitartrate, sorbitan ditartrate, sorbitan tritartrate, sorbitan monocitrate, sorbitan sesquicitrate, sorbitan dicitrate, sorbitan tricitrate, sorbitan monomaleate, sorbitan sesquimaleate, sorbitan dimaleate, sorbitan trimaleate and technical mixtures thereof. Addition products of 1 to 30 and preferably 5 to 10 moles of ethylene oxide with the sorbitan esters mentioned are also suitable.

Typical examples of suitable polyglycerol esters are Polyglyceryl-2 Dipolyhydroxystearate (Dehymuls® PGPH), Polyglycerin-3-Diisostearate (Lameform® TGI), Polyglyceryl-4 Isostearate (Isolan® GI 34), Polyglyceryl-3 Oleate, Diisostearoyl Polyglyceryl-3 Diisostearate (Isolan® PDI), Polyglyceryl-3 Methylglucose Distearate (Tego Care® 450), Polyglyceryl-3 Beeswax (Cera Bellina®), Polyglyceryl-4 Caprate (Polyglycerol Caprate T2010/90), Polyglyceryl-3 Cetyl Ether (Chimexane® NL), Polyglyceryl-3 Distearate (Cremophor® GS 32) and Polyglyceryl Polyricinoleate (Admul® WOL 1403), Polyglyceryl Dimerate Isostearate and mixtures thereof.

Examples of other suitable polyolesters are the mono-, di- and triesters of trimethylol propane or pentaerythritol with lauric acid, cocofatty acid, tallow fatty acid, palmitic acid, stearic acid, oleic acid, behenic acid and the like optionally reacted with 1 to 30 moles of ethylene oxide.

Other suitable emulsifiers are zwitterionic surfactants. Zwitterionic surfactants are surface-active compounds which contain at least one quaternary ammonium group and at least one carboxylate and one sulfonate group in the molecule. Particularly suitable zwitterionic surfactants are the so-called betaines, such as the N-alkyl-N,N-dimethyl ammonium glycinates, for example cocoalkyl dimethyl ammonium glycinate, N-acylaminopropyl-N,N-dimethyl ammonium glycinates, for example cocoacylaminopropyl dimethyl ammonium glycinate, and 2-alkyl-3-carboxymethyl-3-hydroxyethyl imidazolines containing 8 to 18 carbon atoms in the alkyl or acyl group and cocoacylaminoethyl hydroxyethyl carboxymethyl glycinate. The fatty acid amide derivative known under the CTFA name of *Cocamidopropyl Betaine* is particularly preferred. Ampholytic surfactants are also suitable emulsifiers. Ampholytic surfactants are surface-active compounds which, in addition to a $C_{8/18}$ alkyl or acyl group, contain at least one free amino group and at least one —COOH—or —SO$_3$H— group in the molecule and which are capable of forming inner salts. Examples of suitable ampholytic surfactants are N-alkyl glycines, N-alkyl propionic acids, N-alkylaminobutyric acids, N-alkyliminodipropionic acids, N-hydroxyethyl-N-alkylamidopropyl glycines, N-alkyl taurines, N-alkyl sarcosines, 2-alkylaminopropionic acids and alkylaminoacetic acids containing around 8 to 18 carbon atoms in the alkyl group. Particularly preferred ampholytic surfactants are N-cocoalkylaminopropionate, cocoacylaminoethyl aminopropionate and $C_{12/18}$ acyl sarcosine.

Finally, other suitable emulsifiers are cationic surfactants, those of the esterquat type, preferably methyl-quaternized difatty acid triethanolamine ester salts, being particularly preferred.

Suitable solubilizers or hydrotropes are, for example ethanol, isopropyl alcohol or polyols. Suitable polyols preferably contain 2 to 15 carbon atoms and at least two hydroxyl groups. The polyols may contain other functional groups, more especially amino groups, or may be modified with nitrogen. Typical examples are glycerol;

alkylene glycols such as, for example, ethylene glycol, diethylene glycol, propylene glycol, butylene glycol, hexylene glycol and polyethylene glycols with an average molecular weight of 100 to 1000 dalton;

technical oligoglycerol mixtures with a degree of self-condensation of 1.5 to 10 such as, for example, technical diglycerol mixtures with a diglycerol content of 40 to 50% by weight;

methylol compounds such as, in particular, trimethylol ethane, trimethylol propane, trimethylol butane, pentaerythritol and dipentaerythritol;

lower alkyl glucosides, particularly those containing 1 to 8 carbon atoms in the alkyl group, for example methyl and butyl glucoside;

sugar alcohols containing 5 to 12 carbon atoms, for example sorbitol or mannitol, sugars containing 5 to 12 carbon atoms, for example glucose or sucrose;

amino sugars, for example glucamine;

dialcoholamines, such as diethanolamine or 2-aminopropane-1,3-diol.

The concentration of emulsifiers may be in the range from 1 to 20% by weight and is preferably in the range from 5 to 10% by weight, based on the active principles. The quantity of solubilizers is determined solely by the solubility or dispersibility of the active principles in water.

After its preparation from gel former, anionic polymer and active principle, the matrix is very finely dispersed in an oil phase with intensive shearing in order to produce small particles in the subsequent encapsulation process. It has proved to be particularly advantageous in this regard to heat the matrix to temperatures in the range from 40 to 60° C. while the oil phase is cooled to 10 to 20° C. The actual encapsulation, i.e. formation of the membrane by contacting the anionic polymers in the matrix with the (cationic) chitosans, takes place in the third step. To this end, it is advisable to wash the matrix dispersed in the oil phase with an aqueous ca. 0.1 to 3 and preferably 0.25 to 0.5% by weight aqueous solution of the chitosan, preferably a chitosan glycolate, at a temperature in the range from 40 to 100 and preferably 50 to 60° C. and, at the same time, to remove the oil phase. The resulting aqueous preparations generally have a microcapsule content of 1 to 10% by weight. In some cases, it can be of advantage for the solution of the polymers to contain other ingredients, for example emulsifiers or preservatives. After filtration, microcapsules with a mean diameter of preferably 1 to 3 mm are obtained. It is advisable to sieve the capsules to ensure a uniform size distribution. The microcapsules thus obtained may have any shape within production-related limits, but are preferably substantially spherical.

Cosmetic and/or Pharmaceutical Preparations

The microcapsules according to the present invention are intended for the production of surface-active compositions and, in a first embodiment, particularly for the production of cosmetic and/or pharmaceutical preparations such as, for example, hair shampoos, hair lotions, foam baths, shower baths, creams, gels, lotions, alcoholic and aqueous/alcoholic solutions, emulsions, wax/fat compounds, stick preparations, powders or ointments. These preparations may also contain mild surfactants, oil components, emulsifiers, superfatting agents, pearlizing waxes, consistency factors, thickeners, polymers, silicone compounds, fats, waxes, stabilizers, biogenic agents, deodorizers, antiperspirants, antidandruff agents, film formers, swelling agents, UV protection factors, antioxidants, hydrotropes, preservatives, insect repellents, self-tanning agents, solubilizers, perfume oils, dyes and the like as further auxiliaries and additives. Many of these auxiliaries were discussed in detail in earlier paragraphs so that they need not be repeated here.

Typical examples of suitable mild, i.e. particularly dermatologically compatible, surfactants are fatty alcohol polyglycol ether sulfates, monoglyceride sulfates, mono- and/or dialkyl sulfosuccinates, fatty acid isethionates, fatty acid sarcosinates, fatty acid taurides, fatty acid glutamates, α-olefin sulfonates, ether carboxylic acids, alkyl oligoglucosides, fatty acid glucamides, alkylamidobetaines and/or protein fatty acid condensates, preferably based on wheat proteins.

Superfatting agents may be selected from such substances as, for example, lanolin and lecithin and also polyethoxylated or acylated lanolin and lecithin derivatives, polyol fatty acid esters, monoglycerides and fatty acid alkanolamides, the fatty acid alkanolamides also serving as foam stabilizers.

The consistency factors mainly used are fatty alcohols or hydroxyfatty alcohols containing 12 to 22 and preferably 16 to 18 carbon atoms and also partial glycerides, fatty acids or hydroxyfatty acids. A combination of these substances with alkyl oligoglucosides and/or fatty acid N-methyl glucamides of the same chain length and/or polyglycerol poly-12-hydroxystearates is preferably used.

Suitable thickeners are, for example, Aerosil® types (hydrophilic silicas), polysaccharides, more especially xanthan gum, guar guar, agar agar, alginates and tyloses, carboxymethyl cellulose and hydroxyethyl cellulose, also relatively high molecular weight polyethylene glycol monoesters and diesters of fatty acids, polyacrylates (for example Carbopols® [Goodrich] or Synthalens® [Sigma]), polyacrylamides, polyvinyl alcohol and polyvinyl pyrrolidone, surfactants such as, for example, ethoxylated fatty acid glycerides, esters of fatty acids with polyols, for example pentaerythritol or trimethylol propane, narrow-range fatty alcohol ethoxylates or alkyl oligoglucosides and electrolytes, such as sodium chloride and ammonium chloride.

Suitable cationic polymers are, for example, cationic cellulose derivatives such as, for example, the quaternized hydroxyethyl cellulose obtainable from Amerchol under the name of Polymer JR 400®, cationic starch, copolymers of diallyl ammonium salts and acrylamides, quaternized vinyl pyrrolidone/vinyl imidazole polymers such as, for example, Luviquat® (BASF), condensation products of polyglycols and amines, quaternized collagen polypeptides such as, for example, Lauryldimonium Hydroxypropyl Hydrolyzed Collagen (Lamequat® L, Grünau), quaternized wheat polypeptides, polyethyleneimine, cationic silicone polymers such as, for example, amodimethicone, copolymers of adipic acid and dimethylaminohydroxypropyl diethylenetriamine (Cartaretine®), Sandoz), copolymers of acrylic acid with dimethyl diallyl ammonium chloride (Merquat® 550, Chemviron), polyaminopolyamides as described, for example, in FR 2 252 840 A and crosslinked water-soluble polymers thereof, cationic chitin derivatives such as, for example, quaternized chitosan, optionally in microcrystalline distribution, condensation products of dihaloalkyls, for example dibromobutane, with bis-dialkylamines, for example bis-dimethylamino-1, 3-propane, cationic guar gum such as, for example, Jaguar®CBS, Jaguar®C-17, Jaguar®C-16 of Celanese, quaternized ammonium salt polymers such as, for example, Mirapol® A-15, Mirapol® AD-1, Mirapol® AZ-1 of Miranol.

Suitable anionic, zwitterionic, amphoteric and nonionic polymers are, for example, vinyl acetate/crotonic acid copolymers, vinyl pyrrolidone/vinyl acrylate copolymers, vinyl acetate/butyl maleate/isobornyl acrylate copolymers, methyl vinylether/maleic anhydride copolymers and esters thereof, uncrosslinked and polyol-crosslinked polyacrylic acids, acrylamidopropyl trimethylammonium chloride/acrylate copolymers, octylacrylamide/methyl methacrylate/tert.-butylaminoethyl methacrylate/2-hydroxypropyl methacrylate copolymers, polyvinyl pyrrolidone, vinyl pyrrolidone/vinyl acetate copolymers, vinyl pyrrolidone/dimethylaminoethyl methacrylate/vinyl caprolactam terpolymers and optionally derivatized cellulose ethers and silicones.

Suitable silicone compounds are, for example, dimethyl polysiloxanes, methylphenyl polysiloxanes, cyclic silicones and amino-, fatty acid-, alcohol-, polyether-, epoxy-, fluorine-, glycoside- and/or alkyl-modified silicone compounds which may be both liquid and resin-like at room temperature. Other suitable silicone compounds are simethicones which are mixtures of dimethicones with an average chain length of 200 to 300 dimethylsiloxane units and hydrogenated silicates. A detailed overview of suitable volatile silicones can be found in Todd et al. in Cosm. Toil. 91, 27 (1976).

Typical examples of fats are glycerides while suitable waxes are inter alia natural waxes such as, for example, candelilla wax, carnauba wax, Japan wax, espartograss wax, cork wax, guaruma wax, rice oil wax, sugar cane wax, ouricury wax, montan wax, beeswax, shellac wax, spermaceti, lanolin (wool wax), uropygial fat, ceresine, ozocerite (earth wax), petrolatum, paraffin waxes, microwaxes; chemically modified waxes (hard waxes) such as, for example, montan ester waxes, sasol waxes, hydrogenated jojoba waxes and synthetic waxes such as, for example, polyalkylene waxes and polyethylene glycol waxes.

The total percentage content of auxiliaries and additives may be from 1 to 50% by weight and is preferably from 5 to 40% by weight, based on the particular formulation. The formulations may be produced by standard hot or cold processes and are preferably produced by the phase inversion temperature method.

Detergent Preparations

In another embodiment of the present invention, the microcapsules are used for the production of detergents, especially laundry detergents, <dishwashing detergents, cleaning compositions and fabric softeners, in which they may also be present in quantities of 0.1 to 99% by weight and preferably in quantities of 1 to 5% by weight, based on the preparations. The detergents in question are preferably aqueous or aqueous/alcoholic preparations. These liquid detergents may have a non-aqueous component of 5 to 50% by weight and preferably 15 to 35% by weight. In the most simple case, they are aqueous solutions of the surfactant mixtures mentioned. However, the liquid detergents may also be substantially water-free compositions. "Substantially water-free" in the context of the present invention means that the composition preferably contains no free water which is not bound as water of crystallization or in a comparable form. In some cases, small quantities of free water are tolerable, more particularly quantities of up to 5% by weight. The compositions used in the detergent field may contain other typical ingredients such as, for example, solvents, hydrotropes, bleaching agents, builders, viscosity adjusters, enzymes, enzyme stabilizers, optical brighteners, soil repellents, foam inhibitors, inorganic salts and perfumes and dyes, with the proviso that these additives are sufficiently stable in storage in the aqueous medium. Here, too, many of the auxiliaries mentioned were discussed in earlier paragraphs so that there is no need to repeat them.

Suitable organic solvents are, for example, monohydric and/or polyhydric alcohols containing 1 to 6 carbon atoms and preferably 1 to 4 carbon atoms. Preferred alcohols are ethanol, propane-1,2-diol, glycerol and mixtures thereof. The detergents preferably contain 2 to 20% by weight and more preferably 5 to 15% by weight of ethanol or a mixture of ethanol and propane-1,2-diol or, more particularly, of ethanol and glycerol. In another possible embodiment, the preparations contain polyethylene glycol with a relative molecular weight of 200 to 2,000 and preferably up to 600 in quantities of 2 to 17% by weight either in addition to the monohydric and/or polyhydric alcohols containing 1 to 6 carbon atoms or on its own. Suitable hydrotropes are, for example, toluene sulfonate, xylene sulfonate, cumene sulfonate or mixtures thereof.

Suitable builders are ethylenediamine tetraacetic acid, nitrilotriacetic acid, citric acid and inorganic phosphonic acids such as, for example, the neutrally reacting sodium salts of 1-hydroxyethane-1,1-diphosphonate which may be present in quantities of 0.5 to 5% by weight and preferably 1 to 2% by weight.

Suitable viscosity adjusters are, for example, hydrogenated castor oil, salts of long-chain fatty acids, which are preferably used in quantities of 0 to 5% by weight and more preferably in quantities of 0.5 to 2% by weight, for example sodium, potassium, aluminium, magnesium and titanium stearates or the sodium and/or potassium salts of behenic acid, and other polymeric compounds. Preferred other polymeric compounds include polyvinyl pyrrolidone, urethanes and the salts of polymeric polycarboxylates, for example homopolymeric or copolymeric polyacrylates, polymethacrylates and, in particular, copolymers of acrylic acid with maleic acid, preferably those of 50% to 10% maleic acid. The relative molecular weight of the homopolymers is generally between 1,000 and 100,000 while the relative molecular weight of the copolymers is between 2,000 and 200,000 and preferably between 50,000 and 120,000, based on the free acid. Water-soluble polyacrylates which are crosslinked, for example, with about 1% of a polyallyl ether of sucrose and which have a relative molecular weight above 1,000,000 are also particularly suitable. Examples include the polymers with a thickening effect obtainable under the name of Carbopol® 940 and 941. The crosslinked polyacrylates are preferably used in quantities of not more than 1% by weight and more preferably in quantities of 0.2 to 0.7% by weight. The detergents may additionally contain about 5 to 20% by weight of a partly esterified copolymer of the type described in European patent application EP 0 367 049 A. These partly esterified polymers are obtained by copolymerization of (a) at least one $C_{4-28}$ olefin or mixtures of at least one $C_{4-28}$ olefin with up to 20 mole-% of $C_{1-28}$ alkyl vinyl ethers and (b) ethylenically unsaturated dicarboxylic anhydrides containing 4 to 8 carbon atoms in a molar ratio of 1:1 to form copolymers with K values of 6 to 100 and subsequent partial esterification of the copolymers with reaction products, such as $C_{1-13}$ alcohols, $C_{8-22}$ fatty acids, $C_{1-12}$ alkyl phenols, secondary $C_{2-30}$ amines or mixtures thereof, with at least one $C_{2-4}$ alkylene oxide or tetrahydrofuran and hydrolysis of the anhydride groups of the copolymers to carboxyl groups, the partial esterification of the copolymers being continued to such an extent that 5 to 50% of the carboxyl groups of the copolymers are esterified. Preferred copolymers contain maleic anhydride as the ethylenically unsaturated dicarboxylic anhydride. The partly esterified copolymers may be present either in the form of the free acid or preferably in partly or completely neutralized form. The copolymers are advantageously used in the form of an aqueous solution, more particularly in the form of a 40 to 50% by weight solution. The copolymers not only contribute towards the single wash cycle and multiple wash cycle performance of the liquid detergent, they also promote a desirable reduction in viscosity of the concentrated liquid detergents. By using these partly esterified copolymers, it is possible to obtain concentrated aqueous liquid detergents which flow under the sole effect of gravity, i.e. without any need for other shear forces. In a preferred embodiment, the concentrated aqueous liquid detergents contain partly esterified copolymers in quantities of 5 to 15% by weight and, more particularly, in quantities of 8 to 12% by weight.

Suitable soil repellents are polymers which preferably contain ethylene terephthalate and/or polyethylene glycol terephthalate groups, the molar ratio of ethylene terephthalate to polyethylene glycol terephthalate being in the range from 50:50 to 90:10. The molecular weight of the linking polyethylene glycol units is more particularly in the range from 750 to 5,000, i.e. the degree of ethoxylation of the polymers containing polyethylene glycol groups may be about 15 to 100. The polymers are distinguished by an average molecular weight of about 5,000 to 200,000 and may have a block structure, but preferably have a random structure. Preferred polymers are those with molar ethylene terephthalate: polyethylene glycol terephthalate ratios of about 65:35 to about 90:10 and preferably in the range from about 70:30 to 80:20. Other preferred polymers are those which contain linking polyethylene glycol units with a molecular weight of 750 to 5,000 and preferably in the range from 1,000 to about 3,000 and which have a molecular weight of the polymer of about 10,000 to about 50,000. Examples of commercially available polymers are the products Milease® T (ICI) or Repelotex® SRP 3 (Rhone-Poulenc).

Where the detergents are used in washing machines, it can be of advantage to add conventional foam inhibitors to them. Suitable foam inhibitors are, for example, soaps of natural or synthetic origin which have a high percentage of $C_{18-24}$ fatty acids. Suitable non-surface-active foam inhibitors are, for example, organopolysiloxanes and mixtures thereof with microfine, optionally silanized silica and paraffins, waxes, microcrystalline waxes and mixtures thereof with silanized silica or bis-stearyl ethylenediamide. Mixtures of various foam inhibitors, for example mixtures of silicones, paraffins or waxes, may also be used with advantage. The foam inhibitors, more particularly silicone- or paraffin-containing foam inhibitors, are preferably fixed to a granular water-soluble or water-dispersible carrier/support. Mixtures of paraffins and bis-stearyl ethylenediamides are particularly preferred.

The pH value of the detergents is generally in the range from 7 to 10.5, preferably in the range from 7 to 9.5 and more preferably in the range from 7 to 8.5. Higher pH values, for example above 9, can be adjusted by using small quantities of sodium hydroxide or alkaline salts, such as sodium carbonate or sodium silicate. The liquid detergents generally have viscosities of 150 to 10,000 mPas (Brookfield viscosimeter, spindle 1, 20 r.p.m., 20° C.). The substantially water-free detergents preferably have viscosities of 150 to 5,000 mPas. The viscosity of aqueous detergents is preferably below 2,000 mPas and, more particularly, in the range from 150 to 1,000 mPas.

In a final embodiment, microcapsules charged with aromas, for example, are suitable for the production of foods.

EXAMPLES

Example 1

In a 500 ml three-necked flask equipped with a stirrer and reflux condenser, 3 g of agar agar were dissolved in 200 ml water in boiling heat. First a homogeneous disperson of 10 g of glycerol and 2 g of talcum in ad 100 g water and then a preparation of 0.5 g of sodium alginate, 10 g of paraffin oil, 0.5 g of Phenonip® (preservative mixture containing phenoxyethanol and parabens) and 0.5 g of Polysorbate-20 (Tween® 20, ICI) in ad 100 g water were added to the mixture over a period of about 30 mins. with vigorous stirring. The matrix obtained was filtered, heated to 50° C. and dispersed with vigorous stirring in 2.5 times its volume of paraffin oil cooled beforehand to 15° C. The dispersion was then washed with an aqueous solution containing 1% by weight of sodium lauryl sulfate and 0.5% by weight of chitosan (Hydagen® DCMF, Henkel KGaA) and then repeatedly with a 0.5% by weight aqueous Phenonip solution, the oil phase being removed in the process. An aqueous preparation containing 8% by weight of microcapsules with a mean diameter of 1 mm was obtained after sieving.

Example 2

In a 500 ml three-necked flask equipped with a stirrer and reflux condenser, 3 g of agar agar were dissolved in 200 ml water in boiling heat. First a homogeneous disperson of 10 g of glycerol and 2 g of talcum in ad 100 g water and then a preparation of 0.5 g of sodium alginate, 10 g of squalane, 0.5 g of Phenonip® and 0.5 g of Ceteareth-20 in ad 100 g water were added to the mixture over a period of about 30 mins. with vigorous stirring. The matrix obtained was filtered, heated to 50° C. and dispersed with vigorous stirring in 2.5 times its volume of paraffin oil cooled beforehand to 15° C. The dispersion was then washed with an aqueous solution containing 1% by weight of sodium lauryl sulfate and 0.5% by weight of chitosan (Hydagen® DCMF, Henkel KGaA) and then repeatedly with a 0.5% by weight aqueous Phenonip solution, the oil phase being removed in the process. An aqueous preparation containing 8% by weight of microcapsules with a mean diameter of 1 mm was obtained after sieving.

Example 3

In a 500 ml three-necked flask equipped with a stirrer and reflux condenser, 3 g of agar agar were dissolved in 200 ml water in boiling heat. First a homogeneous disperson of 10 g of glycerol and 2 g of iron(II) oxide in ad 100 g water and then a preparation of 0.5 g of sodium alginate, 10 g of panthenol and 0.5 g of Phenonip® in ad 100 g water were added to the mixture over a period of about 30 mins. with vigorous stirring. The matrix obtained was filtered, heated to 50° C. and dispersed with vigorous stirring in 3 times its volume of soybean oil cooled beforehand to 15° C. The dispersion was then washed with an aqueous solution containing 1% by weight of sodium lauryl sulfate and 0.5% by weight of chitosan (Hydagen® DCMF, Henkel KGaA) and then repeatedly with a 0.5% by weight aqueous Phenonip solution, the oil phase being removed in the process. An aqueous preparation containing 8% by weight of microcapsules with a mean diameter of 1 mm was obtained after sieving.

Example 4

In a 500 ml three-necked flask equipped with a stirrer and reflux condenser, 3 g of agar agar were dissolved in 200 ml water in boiling heat. First a homogeneous disperson of 10 g of glycerol and 2 g of talcum in ad 100 g water and then a preparation of 0.5 g of sodium alginate, 10 g of β-carotene and 0.5 g of Phenonip® in ad 100 g water were added to the mixture over a period of about 30 mins. with vigorous stirring. The matrix obtained was filtered, heated to 50° C. and dispersed with vigorous stirring in 2.5 times its volume of soybean oil cooled beforehand to 15° C. The dispersion was then washed with an aqueous solution containing 1% by weight of sodium lauryl sulfate and 0.5% by weight of chitosan (Hydagen® DCMF, Henkel KGaA) and then repeatedly with a 0.5% by weight aqueous Phenonip solution, the oil phase being removed in the process. An aqueous preparation containing 8% by weight of microcapsules with a mean diameter of 1 mm was obtained after sieving.

Example 5

In a 500 ml three-necked flask equipped with a stirrer and reflux condenser, 3 g of agar agar were dissolved in 200 ml water in boiling heat. First a homogeneous disperson of 10 g of glycerol and 2 g of iron(II) oxide in ad 100 g water and then a preparation of 0.5 g of sodium alginate, 10 g of tocopherol acetate and 0.5 g of Phenonip® in ad 100 g water were added to the mixture over a period of about 30 mins. with vigorous stirring. The matrix obtained was filtered, heated to 50° C. and dispersed with vigorous stirring in twice its volume of dicarylyl ether cooled beforehand to 15° C. The dispersion was then washed with an aqueous solution containing 1% by weight of sodium lauryl sulfate and 0.5% by weight of chitosan (Hydagen® DCMF, Henkel KGaA) and then repeatedly with a 0.5% by weight aqueous Phenonip solution, the oil phase being removed in the process. An aqueous preparation containing 8% by weight of microcapsules with a mean diameter of 1 mm was obtained after sieving.

Example 6

In a 500 ml three-necked flask equipped with a stirrer and reflux condenser, 3 g of agar agar were dissolved in 200 ml water in boiling heat. First a homogeneous disperson of 10 g of glycerol and 2 g of iron(II) oxide in ad 100 g water and then a preparation of 0.5 g of sodium alginate, 10 g of ascorbic acid and 0.5 g of Phenonip® in ad 100 g water were added to the mixture over a period of about 30 mins. with vigorous stirring. The matrix obtained was filtered, heated to 50° C. and dispersed with vigorous stirring in 2.5 times its volume of Cocoglycerides cooled beforehand to 15° C. The dispersion was then washed with an aqueous solution containing 1% by weight of sodium lauryl sulfate and 0.5% by weight of chitosan (Hydagen® DCMF, Henkel KGaA) and then repeatedly with a 0.5% by weight aqueous Phenonip solution, the oil phase being removed in the process. An aqueous preparation containing 8% by weight of microcapsules with a mean diameter of 1 mm was obtained after sieving.

Example 7

In a 500 ml three-necked flask equipped with a stirrer and reflux condenser, 3 g of agar agar were dissolved in 200 ml water in boiling heat. First a homogeneous disperson of 10 g of glycerol and 2 g of iron(II) oxide in ad 100 g water and then a preparation of 0.5 g of sodium alginate, 10 g of koji acid and 0.5 g of Phenonip® in ad 100 g water were added to the mixture over a period of about 30 mins. with vigorous stirring. The matrix obtained was filtered, heated to 50° C. and dispersed with vigorous stirring in 4 times its volume of oleyl oleate cooled beforehand to 15° C. The dispersion was then washed with an aqueous solution containing 1% by weight of sodium lauryl sulfate and 0.5% by weight of chitosan (Hydagen® DCMF, Henkel KGaA) and then repeatedly with a 0.5% by weight aqueous Phenonip solution, the oil phase being removed in the process. An aqueous preparation containing 8% by weight of microcapsules with a mean diameter of 1 mm was obtained after sieving.

Example 8

In a 500 ml three-necked flask equipped with a stirrer and reflux condenser, 3 g of agar agar were dissolved in 200 ml water in boiling heat. First a homogeneous disperson of 10 g of glycerol and 2 g of iron(II) oxide in ad 100 g water and then a preparation of 0.5 g of sodium alginate, 10 g of Dehyquart F®) 75 (Distearoylethyl Hydroxyethylmonium Methosulfate and Cetearyl Alcohol, Henkel KGaA) and 0.5 g of Phenonip® in ad 100 g water were added to the mixture over a period of about 30 mins. with vigorous stirring. The matrix obtained was filtered, heated to 50° C. and dispersed with vigorous stirring in 2.5 times its volume of octyl dodecanol cooled beforehand to 15° C. The dispersion was then washed with an aqueous solution containing 1% by weight of sodium lauryl sulfate and 0.5% by weight of chitosan (Hydagen® DCMF, Henkel KGaA) and then repeatedly with a 0.5% by weight aqueous Phenonip solution, the oil phase being removed in the process. An aqueous preparation containing 8% by weight of microcapsules with a mean diameter of 1 mm was obtained after sieving.

Example 9

In a 500 ml three-necked flask equipped with a stirrer and reflux condenser, 3 g of gelatine were dissolved in 200 ml water in boiling heat. First a homogeneous disperson of 10 g of glycerol and 2 g of iron(II) oxide in ad 100 g water and then a preparation of 0.5 g of Hydagen® SCD (succinylated chitosan, Henkel KGaA), 10 g of Dehyquart F® 75 (Distearoylethyl Hydroxyethylmonium Methosulfate and Cetearyl Alcohol, Henkel KGaA) and 0.5 g of Phenonip® in ad 100 g water were added to the mixture over a period of about 30 mins. with vigorous stirring. The matrix obtained was filtered, heated to 50° C. and dispersed with vigorous stirring in 2.5 times its volume of paraffin oil cooled beforehand to 15° C. The dispersion was then washed with an aqueous solution containing 1% by weight of sodium lauryl sulfate and 0.5% by weight of chitosan (Hydagen® DCMF, Henkel KGaA) and then repeatedly with a 0.5% by weight aqueous Phenonip solution, the oil phase being removed in the process. An aqueous preparation containing 8% by weight of microcapsules with a mean diameter of 1 mm was obtained after sieving.

Formulation Examples are set out in Table 1 below.

TABLE 1

Cosmetic preparations (water, preservative to 100% by weight)

| Composition (INCI) | 1 | 2 | 3 | 4 | 5 | 6 | 7 | 8 | 9 | 10 |
|---|---|---|---|---|---|---|---|---|---|---|
| Texapon ® NSO<br>Sodium Laureth Sulfate | — | — | — | — | — | — | 38.0 | 38.0 | 25.0 | — |
| Texapon ® SB 3<br>Disodium Laureth Sulfosuccinate | — | — | — | — | — | — | — | — | 10.0 | — |
| Plantacare ® 818<br>Coco Glucosides | — | — | — | — | — | — | 7.0 | 7.0 | 6.0 | — |
| Plantacare ® PS 10<br>Sodium Laureth Sulfate (and) Coco Glucosides | — | — | — | — | — | — | — | — | — | 16.0 |
| Dehyton ® PK 45<br>Cocamidopropyl Betaine | — | — | — | — | — | — | — | — | 10.0 | — |
| Dehyquart ® A<br>Cetrimonium Chloride | 2.0 | 2.0 | 2.0 | 2.0 | 4.0 | 4.0 | — | — | — | — |
| Dehyquart L ® 80<br>Dococoylmethylethoxymonium Methosulfate (and) Propyleneglycol | 1.2 | 1.2 | 1.2 | 1.2 | 0.6 | 0.6 | — | — | — | — |
| Eumulgin ® B2<br>Ceteareth-20 | 0.8 | 0.8 | — | 0.8 | — | 1.0 | — | — | — | — |
| Eumulgin ® VL 75<br>Lauryl Glucoside (and) Polyglyceryl-2 Polyhydroxystearate (and) Glycerin | — | — | 0.8 | — | 0.8 | — | — | — | — | — |
| Lanette ® O<br>Cetearyl Alcohol | 2.5 | 2.5 | 2.5 | 2.5 | 3.0 | 2.5 | — | — | — | — |
| Cutina ® GMS<br>Glyceryl Stearate | 0.5 | 0.5 | 0.5 | 0.5 | 0.5 | 1.0 | — | — | — | — |
| Cetiol ® HE<br>PEG-7 Glyceryl Cocoate | 1.0 | — | — | — | — | — | — | — | 1.0 | — |
| Cetiol ® PGL<br>Hexyldecanol (and) Hexyldecyl laurate | — | 1.0 | — | — | 1.0 | — | — | — | — | — |
| Cetiol ® V<br>Decyl Oleate | — | — | — | 1.0 | — | — | — | — | — | — |
| Eutanol ® G<br>Octyldodecanol | — | — | 1.0 | — | — | 1.0 | — | — | — | — |
| Nutrilan ® Keratin W<br>Hydrolyzed Keratin | — | — | — | 2.0 | — | — | — | — | — | — |
| Lamesoft ® LMG<br>Glyceryl Laurate (and) Potassium Cocoyl Hydrolyzed Collagen | — | — | — | — | — | — | 3.0 | 2.0 | 4.0 | — |
| Euperlan ® PK 3000 AM<br>Glycol Distearate (and) Laureth-4 (and) Cocamidopropyl Betaine | — | — | — | — | — | — | — | 3.0 | 5.0 | 5.0 |
| Generol ® 122 N<br>Soya Sterol | — | — | — | — | 1.0 | 1.0 | — | — | — | — |
| Panthenol microcapsules of Example 3 | 1.0 | 1.0 | 1.0 | 1.0 | 1.0 | 1.0 | 1.0 | 1.0 | 1.0 | 1.0 |
| Hydagen ® CMF<br>Chitosan | 1.0 | 1.0 | 1.0 | 1.0 | 1.0 | 1.0 | 1.0 | 1.0 | 1.0 | 1.0 |
| Copherol ® 1250<br>Tocopherol Acetate | — | — | 0.1 | 0.1 | — | — | — | — | — | — |
| Arlypon ® F<br>Laureth-2 | — | — | — | — | — | — | 3.0 | 3.0 | 1.0 | — |
| Sodium Chloride | — | — | — | — | — | — | — | 1.5 | — | 1.5 |

| Composition (INCI) | 11 | 12 | 13 | 14 | 15 | 16 | 17 | 18 | 19 | 20 |
|---|---|---|---|---|---|---|---|---|---|---|
| Texapon ® NSO<br>Sodium Laureth Sulfate | 20.0 | 20.0 | 12.4 | — | 25.0 | 11.0 | — | — | — | — |
| Texpon ® K 14 S<br>Sodium Myreth Sulfate | — | — | — | — | — | — | — | — | 11.0 | 23.0 |
| Texapon ® SB 3<br>Disodium Laureth Sulfosuccinate | — | — | — | — | — | 7.0 | — | — | — | — |
| Plantacare ® 818<br>Coco Glucosides | 5.0 | 5.0 | 4.0 | — | — | — | — | — | 6.0 | 4.0 |
| Plantacare ® 2000<br>Decyl Glucoside | — | — | — | — | 5.0 | 4.0 | — | — | — | — |
| Plantacare ® PS 10<br>Sodium Laureth Sulfate (and) Coco Glucosides | — | — | — | 40.0 | — | — | 16.0 | 17.0 | — | — |
| Dehyton ® PK 45<br>Cocamidopropyl Betaine | 20.0 | 20.0 | — | — | 8.0 | — | — | — | — | 7.0 |
| Eumulgin ® B1<br>Ceteareth-12 | — | — | — | 1.0 | — | — | — | — | — | — |
| Eumulgin ® B2<br>Ceteareth-20 | — | — | — | 1.0 | — | — | — | — | — | — |
| Lameform ® TGI<br>Polyglyceryl-3 Isostearate | — | — | — | 4.0 | — | — | — | — | — | — |

TABLE 1-continued

| Cosmetic preparations (water, preservative to 100% by weight) | | | | | | | | | | |
|---|---|---|---|---|---|---|---|---|---|---|
| Dehymuls ® PGPH<br>Polyglyceryl-2 Dipolyhydroxystearate | — | — | 1.0 | — | — | — | — | — | — | — |
| Monomuls ® 90-L 12<br>Glyceryl Laurate | — | — | — | — | — | — | — | — | 1.0 | 1.0 |
| Cetiol ® HE<br>PEG-7 Glyceryl Cocoate | — | 0.2 | — | — | — | — | — | — | — | — |
| Eutanol ® G<br>Octyldodecanol | — | — | — | 3.0 | — | — | — | — | — | — |
| Nutrilan ® Keratin W<br>Hydrolyzed Keratin | — | — | — | — | — | — | — | — | 2.0 | 2.0 |
| Nutrilan ® I<br>Hydrolyzed Collagen | 1.0 | — | — | — | — | 2.0 | — | 2.0 | — | — |
| Lamesoft ® LMG<br>Glyceryl Laurate (and) Potassium Cocoyl Hydrolyzed Collagen | — | — | — | — | — | — | — | — | 1.0 | — |
| Lamesoft ® 156<br>Hydrogenated Tallow Glyceride (and) Potassium Cocoyl Hyrolyzed Collagen | — | — | — | — | — | — | — | — | — | 5.0 |
| Gluadin ® WK<br>Sodium Cocoyl Hydrolyzed Wheat Protein | 1.0 | 1.5 | 4.0 | 1.0 | 3.0 | 1.0 | 2.0 | 2.0 | 2.0 | — |
| Euperlan ® PK 3000 AM<br>Glycol Distearate (and) Laureth-4 (and) Cocamidopropyl Betaine | 5.0 | 3.0 | 4.0 | — | — | — | — | 3.0 | 3.0 | — |
| Arlypon ® F<br>Laureth-2 | 2.6 | 1.6 | — | 1.0 | 1.5 | — | — | — | — | — |
| Panthenol microcapsules of Example 3 | 1.0 | 1.0 | 1.0 | 1.0 | 1.0 | 1.0 | 1.0 | 1.0 | 1.0 | 1.0 |
| Hydagen ® CMF<br>Chitosan | 1.0 | 1.0 | 1.0 | 1.0 | 1.0 | 1.0 | 1.0 | 1.0 | 1.0 | 1.0 |
| Sodium Chloride | — | — | — | — | 1.6 | 2.0 | 2.2 | — | 3.0 | |
| Glycerin (86% by weight) | — | 5.0 | — | — | — | — | — | 1.0 | 3.0 | — |

| Composition (INCI) | 21 | 22 | 23 | 24 | 25 | 26 | 27 | 28 | 29 | 30 |
|---|---|---|---|---|---|---|---|---|---|---|
| Texapon ® NSO<br>Sodium Laureth Sulfate | — | 30.0 | 30.0 | — | 25.0 | — | — | — | — | — |
| Plantacare ® 818<br>Coco Glucosides | — | 10.0 | — | — | 20.0 | — | — | — | — | — |
| Plantacare ® PS 10<br>Sodium Laureth Sulfate (and) Coco Glucosides | 22.0 | — | 5.0 | 22.0 | — | — | — | — | — | — |
| Dehyton ® PK45<br>Cocamidopropyl Betaine | 15.0 | 10.0 | 15.0 | 15.0 | 20.0 | — | — | — | — | — |
| Emulgade ® SE<br>Glyceryl Stearate (and) Ceteareth 12/20 (and) Cetearyl Alcohol (and) Cetyl Palmitate | — | — | — | — | — | 5.0 | 5.0 | 4.0 | — | — |
| Eumulgin ® B1<br>Ceteareth-12 | — | — | — | — | — | — | — | 1.0 | — | — |
| Lameform ® TGI<br>Polyglyceryl-3 Isostearate | — | — | — | — | — | — | — | — | 4.0 | — |
| Dehymuls ® PGPH<br>Polyglyceryl-2 Dipolyhydroxystearate | — | — | — | — | — | — | — | — | — | 4.0 |
| Monomuls ® 90-O 18<br>Glyceryl Oleate | — | — | — | — | — | — | — | — | 2.0 | — |
| Cetiol ® HE<br>PEG-7 Glyceryl Cocoate | 2.0 | — | — | 2.0 | 5.0 | — | — | — | — | 2.0 |
| Cetiol ® OE<br>Dicaprylyl Ether | — | — | — | — | — | — | — | — | 5.0 | 6.0 |
| Cetiol ® PGL<br>Hexyldecanol (and) Hexyldecyl Laurate | — | — | — | — | — | — | — | 3.0 | 10.0 | 9.0 |
| Cetiol ® SN<br>Cetearyl Isononanoate | — | — | — | — | — | 3.0 | 3.0 | — | — | — |
| Cetiol ® V<br>Decyl Oleate | — | — | — | — | — | 3.0 | 3.0 | — | — | — |
| Myritol ® 318<br>Coco Caprylate Caprate | — | — | — | — | — | — | — | 3.0 | 5.0 | 5.0 |
| Bees Wax | — | — | — | — | — | — | — | — | 7.0 | 5.0 |
| Nutrilan ® Elastin E20<br>Hydrolyzed Elastin | — | — | — | — | — | 2.0 | — | — | — | — |
| Nutrilan ® I-50<br>Hydrolyzed Collagen | — | — | — | — | 2.0 | — | 2.0 | — | — | — |
| Gluadin ® AGP<br>Hydrolyzed Wheat Gluten | 0.5 | 0.5 | 0.5 | — | — | — | — | 0.5 | — | — |
| Gluadin ® WK<br>Sodium Cocoyl Hydrolyzed Wheat Protein | 2.0 | 2.0 | 2.0 | 2.0 | 5.0 | — | — | — | 0.5 | 0.5 |
| Euperlan ® PK 3000 AM<br>Glycol Distearate (and) Laureth-4 (and) Cocamidopropyl Betaine | 5.0 | — | — | 5.0 | — | — | — | — | — | — |

TABLE 1-continued

| Cosmetic preparations (water, preservative to 100% by weight) | | | | | | | | | | |
|---|---|---|---|---|---|---|---|---|---|---|
| Arlypon ® F Laureth-2 | — | — | — | — | — | — | — | — | — | — |
| Panthenol microcapsules of Example 3 | 1.0 | 1.0 | 1.0 | 1.0 | 1.0 | 1.0 | 1.0 | 1.0 | 1.0 | 1.0 |
| Hydagen ® CMF Chitosan | 1.0 | 1.0 | 1.0 | 1.0 | 1.0 | 1.0 | 1.0 | 1.0 | 1.0 | 1.0 |
| Magnsium Sulfate Hepta Hydrate | — | — | — | — | — | — | — | — | 1.0 | 1.0 |
| Glycerin (85% by weight) | — | — | — | — | — | 3.0 | 3.0 | 5.0 | 5.0 | 3.0 |
| Composition (INCI) | 31 | 32 | 33 | 34 | 35 | 36 | 37 | 38 | 39 | 40 |
| Dehymuls ® PGPH Polyglyceryl-2 Dipolyhydroxystearate | 4.0 | 3.0 | — | 5.0 | — | — | — | — | — | — |
| Lameform ® TGI Polyglyceryl-3 Diisostearate | 2.0 | 1.0 | — | — | — | — | — | — | — | — |
| Emulgade ® PL 68/50 Cetearyl Glucoside (and) Cetearyl Alcohol | — | — | — | — | 4.0 | — | — | — | 3.0 | — |
| Eumulgin ® B2 Ceteareth-20 | — | — | — | — | — | — | — | 2.0 | — | — |
| Tegocare ® PS Polyglyceryl-3 Methylglucose Distearate | — | — | 3.0 | — | — | — | 4.0 | — | — | — |
| Eumulgin VL 75 Polyglyceryl-2 Dipolyhydroxystearate (and) Lauryl Glucoside (and) Glycerin | — | — | — | — | — | 3.5 | — | — | 2.5 | — |
| Bees Wax | 3.0 | 2.0 | 5.0 | 2.0 | — | — | — | — | — | — |
| Cutina ® GMS Glyceryl Stearate | — | — | — | — | — | 2.0 | 4.0 | — | — | 4.0 |
| Lanette ® O Cetearyl Alcohol | — | — | 2.0 | — | 2.0 | 4.0 | 2.0 | 4.0 | 4.0 | 1.0 |
| Antaron ® V 216 PVP/Hexadecene Copolymer | — | — | — | — | 3.0 | — | — | — | — | 2.0 |
| Myritol ® 818 Cocoglycerides | 5.0 | — | 10.0 | — | 8.0 | 6.0 | 6.0 | — | 5.0 | 5.0 |
| Finsolv ® TN C12/15 Alkyl Benzoate | — | 6.0 | — | 2.0 | — | — | 3.0 | — | — | 2.0 |
| Cetiol ® J 600 Oleyl Erucate | 7.0 | 4.0 | 3.0 | 5.0 | 4.0 | 3.0 | 3.0 | — | 5.0 | 4.0 |
| Cetiol ® OE Dicaprylyl Ether | 3.0 | — | 6.0 | 8.0 | 6.0 | 5.0 | 4.0 | 3.0 | 4.0 | 6.0 |
| Mineral Oil | — | 4.0 | — | 4.0 | — | 2.0 | — | 1.0 | — | — |
| Cetiol ® PGL Hexadecanol (and) Hexyldecyl Laurate | — | 7.0 | 3.0 | 7.0 | 4.0 | — | — | — | 1.0 | — |
| Bisabolol | 1.2 | 1.2 | 1.2 | 1.2 | 1.2 | 1.2 | 1.2 | 1.2 | 1.2 | 1.2 |
| Panthenol microcapsules of Example 3 | 1.0 | 1.0 | 1.0 | 1.0 | 1.0 | 1.0 | 1.0 | 1.0 | 1.0 | 1.0 |
| Hydagen ® CMF Chitosan | 1.0 | 1.0 | 1.0 | 1.0 | 1.0 | 1.0 | 1.0 | 1.0 | 1.0 | 1.0 |
| Copherol ® F 1300 Tocopherol/Tocopheyl Acetate | 0.5 | 1.0 | 1.0 | 2.0 | 1.0 | 1.0 | 1.0 | 2.0 | 0.5 | 2.0 |
| Neo Heliopan ® Hydro Sodium Phenylbenzimidazole Sulfonate | 3.0 | — | — | 3.0 | — | — | 2.0 | — | 2.0 | — |
| Neo Heliopan ® 303 Octocrylene | — | 5.0 | — | — | — | 4.0 | 5.0 | — | — | 10.0 |
| Neo Heliopan ® BB Benzophenone-3 | 1.5 | — | — | 2.0 | 1.5 | — | — | — | 2.0 | — |
| Neo Heliopan ® E 1000 Isoamyl p-Methoxycinnamate | 5.0 | — | 4.0 | — | 2.0 | 2.0 | 4.0 | 10.0 | — | — |
| Neo Heliopan ® AV Octyl Methoxycinnamate | 4.0 | — | 4.0 | 3.0 | 2.0 | 3.0 | 4.0 | — | 10.0 | 2.0 |
| Uvinol ® T 150 Octyl Triazone | 2.0 | 4.0 | 3.0 | 1.0 | 1.0 | 1.0 | 4.0 | 3.0 | 3.0 | 3.0 |
| Zinc Oxide | — | 6.0 | 6.0 | — | 4.0 | — | — | — | — | 5.0 |
| Titanium Dioxide | — | — | — | — | — | — | — | 5.0 | — | — |
| Glycerin (86% by weight) | 5.0 | 5.0 | 5.0 | 5.0 | 5.0 | 5.0 | 5.0 | 5.0 | 5.0 | 5.0 |

(1–4) hair rinse, (5–6) conditioner, (7–8) shower bath, (9) shower gel, (10) wash lotion
(11–14) "two-in-one" shower bath, (15–20) shampoo
(21–25) foam bath, (26) soft cream, (27, 28) moisturizing emulsion, (29, 20) night cream
(31) w/o sun protection cream, (32–34) w/o sun protection lotion, (35, 38, 40) o/w sun protection lotion, (36, 37, 39) o/w sun protection cream

What is claimed is:

1. A microcapsule having a mean diameter of from about 0.1 to about 5 mm, a membrane and a matrix containing at least one active principle wherein the microcapsule is the product of the process comprising the steps of (a) forming an aqueous matrix by heating an aqueous solution comprised of a gel former, an anionic polymer selected from the group consisting of a salt of alginic acid and an anionic chitosan derivative and active principle; (b) forming a dispersed matrix by adding the aqueous matrix in an oil phase; (c) contacting the dispersed matrix with an aqueous solution of chitosan.

2. A process for producing a microcapsule having a mean diameter of from about 0.1 to about 5 mm, a membrane and a matrix containing at least one active principle comprising the steps of (a) forming an aqueous matrix by heating an aqueous solution comprised of a gel former, an anionic polymer selected from the group consisting of a salt of alginic acid and an anionic chitosan derivative, and active principle; (b) forming a dispersed matrix by adding the aqueous matrix in an oil phase; (c) contacting the dispersed matrix with an aqueous solution of chitosan.

3. The process of claim 2 wherein the gel former is a heteropolysaccharide or a protein.

4. The process of claim 3 wherein the heteropolysaccharide is an agarose, agar agar, a pectin, a xanthan and mixtures hereof.

5. The process of claim 3 wherein the protein is gelatine.

6. The process of claim 2 wherein the average molecules weight of the chitosan is from about 10,000 to about 1,200,000 daltons.

7. The process of claim 6 wherein the molecular weight is from about 500,000 to about 800,000 daltons.

8. The process of claim 2 wherein the active principle is selected from the group consisting of a surfactant, a cosmetic oil, a pearlizing wax, a stabilizer, a biogenic agent, a deodorant, an antiperspirant, an antidandruff agent, an UV protection factor, an antioxidant, a preservative, an insect repellent, a self-tanning agent, a perfume oil, a flavor, a bleaching agent, a bleach activator, an enzyme, a redeposition inhibitor, an optical brightener and a dye.

9. The process of claim 2 wherein the amount of active principle in the microcapsule is from about 0.1 to about 25% by weight.

10. The process of claim 2 wherein the matrix is further comprised of an emulsifier, a viscosity adjuster or a combination thereof.

11. The process of claim 2 wherein the process is carried out at a temperature of from about 40 to about 100° C.

12. The process of claim 2 wherein the matrix is dispersed in 2 to 5 times its volume of the oil phase.

13. The process of claim 2 wherein in step (b) the temperature of the matrix is from about 40 to about 60° C. and the temperature of the oil phase is from about 10 to about 20° C.

14. The process of claim 2 wherein the dispersed matrix is added to from about 0.1 to about 3% by weight of an aqueous solution of chitosan.

15. The process of claim 14 wherein the dispersed matrix is contacted at a temperature of from about 40 to about 100° C.

16. The process of claim 15 further comprising step (d) wherein the oil phase is removed.

* * * * *